United States Patent
Lal et al.

(10) Patent No.: US 10,517,626 B2
(45) Date of Patent: Dec. 31, 2019

(54) SEMICONDUCTOR TWEEZERS AND INSTRUMENTATION FOR TISSUE DETECTION AND CHARACTERIZATION

(71) Applicant: Cornell University, Ithaca, NY (US)

(72) Inventors: Amit Lal, Ithaca, NY (US); Fabrizio Michelassi, New York, NY (US); Po-Cheng Chen, Ithaca, NY (US); Connie Wu, Princeton, NJ (US)

(73) Assignee: Cornell University, Ithaca, NY (US)

( * ) Notice: Subject to any disclaimer, the term of this patent is extended or adjusted under 35 U.S.C. 154(b) by 673 days.

(21) Appl. No.: 14/910,660

(22) PCT Filed: Aug. 7, 2014

(86) PCT No.: PCT/US2014/050237
§ 371 (c)(1),
(2) Date: Feb. 5, 2016

(87) PCT Pub. No.: WO2015/021333
PCT Pub. Date: Feb. 12, 2015

(65) Prior Publication Data
US 2016/0174998 A1 Jun. 23, 2016

Related U.S. Application Data

(60) Provisional application No. 61/863,413, filed on Aug. 7, 2013.

(51) Int. Cl.
*A61B 5/00* (2006.01)
*A61B 17/30* (2006.01)
(Continued)

(52) U.S. Cl.
CPC ....... *A61B 17/30* (2013.01); *A61B 2017/0011* (2013.01); *A61B 2017/00026* (2013.01);
(Continued)

(58) Field of Classification Search
CPC ............ A61B 18/1445; A61B 18/1442; A61B 2018/1455; A61B 2018/00601;
(Continued)

(56) References Cited

U.S. PATENT DOCUMENTS 5,464,405 A * 11/1995 Fujitsu ............... A61B 18/1442
606/211
6,048,341 A * 4/2000 Hirakawa .......... A61B 18/1442
606/51
(Continued)

FOREIGN PATENT DOCUMENTS

WO 2012009550 A2 1/2012

OTHER PUBLICATIONS

Chen, P-C. et al., "A Silicon Electro-Mechano Tissue Assay Surgical Tweezer", MEMS, 2014, pp. 13-16.
(Continued)

*Primary Examiner* — May A Abouelela
(74) *Attorney, Agent, or Firm* — Perkins Coie LLP

(57) ABSTRACT

Devices, systems, and techniques are disclosed for intelligent semiconductor based medical tweezers and instrumentation including microscale sensors, actuators and circuitry for tissue detection and characterization. In one aspect, a tweezer device includes a hinge structure to enable tweezing motion of the device for clamping a sample, two leg components coupled to the hinge structure, a plurality of microprobes configured on both of the two leg components, and an electronic circuit electrically coupled to the microprobes to process and/or transmit the electronic signals. The microprobes include sensors in a sensing tip structured to penetrate into the sample when the device clamps the sample and produce electronic signals from the sensors of a property of the sample, the sensors of the sensing tip including at least one of an electrode to measure an electrical potential, an electrical permittivity sensor to measure electrical permittivity, or a strain gauge to measure mechanical compliance.

34 Claims, 20 Drawing Sheets

(51) Int. Cl.
*A61B 17/32* (2006.01)
*A61B 17/00* (2006.01)

(52) U.S. Cl.
CPC .............. *A61B 2017/00221* (2013.01); *A61B 2017/305* (2013.01); *A61B 2017/320093* (2017.08); *A61B 2017/320094* (2017.08); *A61B 2017/320097* (2017.08); *A61B 2560/0214* (2013.01); *A61B 2562/0261* (2013.01)

(58) Field of Classification Search
CPC .............. A61B 2018/126; A61B 18/14; A61B 2018/00875; A61B 2018/1462; A61B 18/085; A61B 2018/1467
USPC .......... 600/300, 547, 552, 587, 595; 606/52, 606/169, 211
See application file for complete search history.

(56) References Cited

U.S. PATENT DOCUMENTS

| | | | | |
|---|---|---|---|---|
| 6,228,084 | B1* | 5/2001 | Kirwan, Jr. | A61B 18/1442 606/51 |
| 6,233,504 | B1* | 5/2001 | Das | B25J 9/1689 414/4 |
| 6,592,583 | B2 | 7/2003 | Hirano et al. | |
| 6,740,058 | B2* | 5/2004 | Lal | A61F 9/00745 604/65 |
| 7,223,267 | B2* | 5/2007 | Isola | A61B 17/320068 606/169 |
| 7,621,911 | B2* | 11/2009 | Ariola, Jr. | A61B 18/1442 606/210 |
| 8,108,994 | B2 | 2/2012 | Ariola, Jr. et al. | |
| 8,197,418 | B2 | 6/2012 | Lal et al. | |
| 8,888,771 | B2* | 11/2014 | Twomey | A61B 17/28 606/41 |
| 2004/0229295 | A1* | 11/2004 | Marchitto | A61M 37/00 435/7.5 |
| 2007/0083119 | A1* | 4/2007 | Adachi | A61B 8/12 600/437 |
| 2008/0009763 | A1 | 1/2008 | Chiou et al. | |
| 2008/0015567 | A1* | 1/2008 | Kimura | A61B 18/1442 606/41 |
| 2008/0125767 | A1* | 5/2008 | Blaha | G01K 7/13 606/34 |
| 2009/0137925 | A1* | 5/2009 | Cantor | A61B 5/053 600/547 |
| 2010/0087814 | A1* | 4/2010 | Desinger | A61B 18/1442 606/45 |
| 2010/0324453 | A1* | 12/2010 | Lal | A61B 5/0053 600/587 |
| 2011/0009899 | A1 | 1/2011 | Picha Muthu et al. | |
| 2011/0166563 | A1* | 7/2011 | Cheng | A61B 18/082 606/30 |
| 2011/0270121 | A1* | 11/2011 | Johnson | A61B 5/0538 600/554 |
| 2011/0275952 | A1* | 11/2011 | Johnson | A61B 18/1233 600/547 |
| 2011/0301607 | A1* | 12/2011 | Couture | A61B 18/1206 606/52 |
| 2012/0172890 | A1* | 7/2012 | Paltieli | A61B 17/44 606/122 |
| 2013/0018371 | A1* | 1/2013 | Twomey | A61B 17/28 606/41 |
| 2013/0103024 | A1* | 4/2013 | Monson | H02J 7/00 606/33 |
| 2013/0226178 | A1* | 8/2013 | Brandt | A61B 18/1442 606/49 |
| 2015/0005768 | A1* | 1/2015 | Sutherland | A61B 18/1442 606/42 |

OTHER PUBLICATIONS

Hammond et al., "Printing Strain Gauges on Surgical Instruments for Force Measurement", Journal of Medical Devices, 2014, vol. 8, pp. 030935-1-030935-2.
International Search Report and Written Opinion for PCT Application No. PCT/US2014/050237, dated Dec. 16, 2014, 7 pages.

* cited by examiner

SEMICONDUCTOR TWEEZERS AND INSTRUMENTATION FOR TISSUE DETECTION AND CHARACTERIZATION

CROSS REFERENCE TO RELATED APPLICATIONS

This patent document is a 35 USC § 371 National Stage application of International Application No. PCT/US2014/050237 filed Aug. 7, 2014, which further claims the benefit of priority of U.S. Provisional Patent Application No. 61/863,413 entitled "MEDICAL TWEEZERS AND SURGICAL TOOLS HAVING BUILT-IN SILICON-BASED MICROSENSORS, MICROACTUATORS, AND SENSING CIRCUITS" filed on Aug. 7, 2013. The entire content of the above patent applications is incorporated by reference as part of the disclosure of this patent document.

STATEMENT REGARDING FEDERALLY SPONSORED RESEARCH OR DEVELOPMENT

This invention was made with government support under grant ECCS-0335765 awarded by the NNIN REU Program funded by the National Science Foundation (NSF). The government has certain rights in the invention.

TECHNICAL FIELD

This patent document relates to systems, devices, and processes that use sensor and actuator technologies.

BACKGROUND

During surgery there are many times that a surgeon would like to identify tissue properties in order to make better decisions about cutting, removing, and sewing tissue. This identification can be based on optical measurements using endoscopes or direct visuals. The identification can also be by palpating the tissue and determining its mechanical properties. Alternatively electrical properties can be used to test tissue properties. One example of such need is that of colon surgery.

SUMMARY

Devices, systems, and techniques are disclosed for intelligent semiconductor based medical tweezers and instrumentation including microscale sensors, actuators and circuitry for tissue detection and characterization.

In one aspect, a tweezer device includes a hinge structure to enable tweezing motion of the device for clamping a sample, two leg components coupled to the hinge structure, a plurality of microprobes configured on both of the two leg components, and an electronic circuit electrically coupled to the microprobes to process and/or transmit the electronic signals. The microprobes include sensors in a sensing tip structured to penetrate into the sample when the device clamps the sample and produce electronic signals from the sensors of a property of the sample, the sensors of the sensing tip including at least one of an electrode to measure an electrical potential, an electrical permittivity sensor to measure electrical permittivity, or a strain gauge to measure mechanical compliance.

In one aspect, a method to characterize a property of biological tissue includes clamping a tissue with a tweezer device comprising a hinge structure to allow tweezing motion of the tweezer device, two leg components attached to the hinge structure, and a plurality of microprobes configured on both of the two leg components to penetrate into the tissue when the tweezer device clamps the sample and produce electric signals associated with at least one property of the tissue; and transferring the electric signals to a remote device.

In one aspect, a semiconductor tweezer device includes a hinge structure to provide a spring for tweezing motion of the semiconductor tweezer device; two leg components coupled to the hinge structure; one or more arm components coupled to the leg components and structured to include an electronic interface unit to transmit detected electronic signals as an RF signal to an RF receiver; an array of microprobes configured at an end of one or both leg components away from the hinge structure and operable to measure mechanical and electrical properties of a sample clamped by the tweezer device, the microprobes structured to include protruding regions comprising electrical permittivity sensors, electrode sensors, and polysilicon strain gauges to provide the detected electronic signals by the microprobe to the electronic interface; a transducer element operable to transmit sonic pulses at the two leg components; and a receiver element operable to receive the transmitted sonic pulses and to determine the distance between the two leg components.

Those and other features are described in greater detail in the drawings, the description and the claims.

DETAILED DESCRIPTION

Figure 1A:
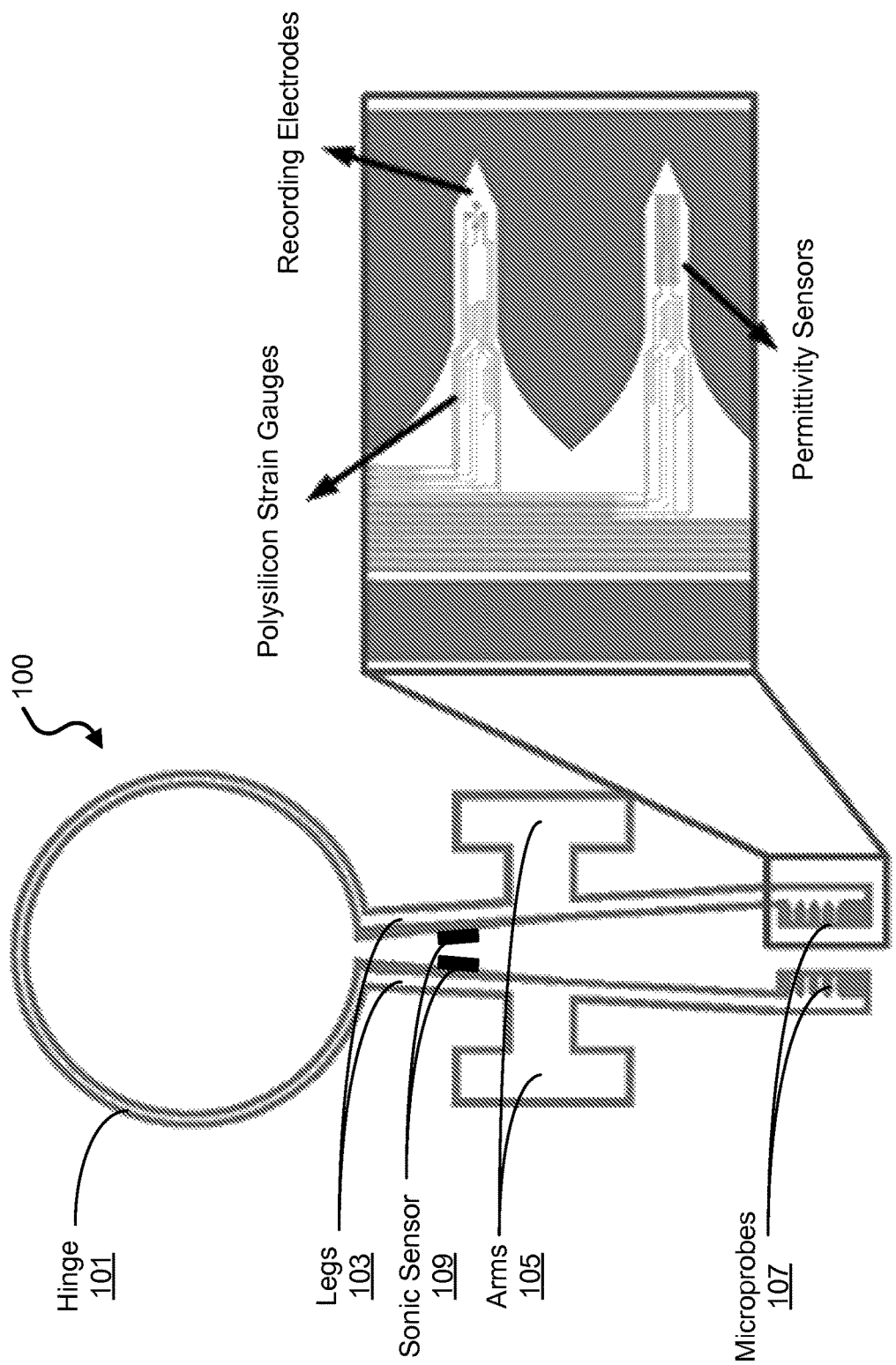
FIGS. 1A-1C show diagrams of exemplary semiconductor tweezer devices of the disclosed technology.

Intestinal anastomosis is the surgical procedure of joining two intestinal loops after removal of a diseased intestinal segment. Currently, intestinal anastomoses are commonly performed with stapling devices. Typically, to compensate for the difference in intestinal wall thickness due to individual patient variability and different pathologic conditions, stapling devices come loaded with staples of different height. For example, the most common staples, when fired, have a profile height that varies between 1.0 mm and 2.0 mm.

Despite the high reliability of stapling devices, medical procedures such as intestinal anastomoses fail to heal appropriately in about 1-7% of cases. This failure is called a dehiscence. Dehiscences are catastrophic events for patients in terms of additional morbidity, the need for additional interventions, increased length of hospital stay and recovery, occasional mortality, and overall increased cost to the health care system. For example, dehiscences can add an average of $30,000 to 50,000 of excess cost to the cost of a simple bowel resection. Intestinal resections and anastomoses are common procedures. In the United States, with more than 500,000 intestinal resection performed each year for cancer, acute and chronic inflammatory bowel disease, hemorrhage, obstruction and congenital malformations, the cost of caring for 1-7% of patients suffering a dehiscence amounts is substantial, and increased health risk and patient morbidity is created.

There are many reasons for the non-healing of tissue after surgeries such as intestinal anastomosis. One reason involves a mismatch between the size of the staplers and the thickness of the intestine. For example, the intestinal wall may be too thick even for the largest staple, causing the mismatch. Another reason for the non-healing of intestinal anastomosis can include a decrease in compliance and pliability of the intestinal wall. For example, the intestinal wall may be too rigid to accept a staple without being fractured.

A device capable of accurately measuring both intestinal wall thickness and mechanical compliance could help surgeons to choose the appropriate size staples or to identify situations where alternative methods to perform an anastomosis should be used, e.g., such as performing a hand-sewn anastomosis, rather than stapled anastomosis. At present, most gastrointestinal surgeries do not use any tissue monitoring devices. Typically, the surgeon's expertise drives the choice of anastomotic technique and, if a stapling device is chosen, the size of the staples to be used.

Devices, systems, and methods are disclosed for intelligent semiconductor based medical tweezers and instrumentation including microscale sensors, actuators and circuitry for tissue detection and characterization.

In one aspect, a semiconductor tweezer device includes a hinge structure to provide a support structure with a spring mechanism for tweezing motion of the semiconductor tweezer device; two leg components coupled to the hinge structure to be at desired relative positions with respect to each other and to be movable relative to each other due to the operation of the spring mechanism to provide the tweezing motion for clamping a sample tissue or object; one or more arm components coupled to the leg components and structured to include an electronic interface to transmit detected electronic signals as an RF signal to an RF receiver; an array of microprobes configured at an end of one or both leg components away from the hinge structure and operable to measure mechanical and electrical properties of a sample clamped by the tweezer device (e.g., including longitudinal force and flexural oscillating motion), the microprobes structured to include protruding regions comprising electrical permittivity sensors, electrode sensors, and polysilicon strain gauges to provide the detected electronic signals by the microprobe to the electronic interface; a transducer element operable to transmit sonic pulses at the two leg components; and a receiver element operable to receive the transmitted sonic pulses and to determine the distance between the two leg components.

In another aspect, the disclosed technology includes a class of sensors that can be integrated within surgical tools that measure tissue stiffness and transmit the data using built-in RF channels.

The disclosed tool-sets may have implications for revolutionizing the choice of the anastomotic technique and technology used by providing measurements of tissue characteristics which better inform a medical practitioner for medical treatment, e.g., such as a surgeon at the time of a surgical procedure. In some aspects, the measurement of tissue stiffness and thickness can allow the proper determination of the tissue suturing technique. For example, by knowing if the tissue is too stiff, too thick or too fragile, hand suturing maybe warranted. With the appropriate tissue thickness, the measurement can indicate what size staples are needed for optimum tissue apposition and healing. These live, real-time measurements can help the surgeon to make better tissue-suturing decisions, which may ultimately reduce the 1-7% postoperative dehiscence rate. The reduction of the dehiscence rate has the potential to spare thousands of patients this catastrophic complication, save millions of dollars to healthcare, and reduce the cost of medical malpractice to hospitals and physicians.

Any new technology has the potential of violating the stringent requirements of the medical environments. The disclosed technology minimizes or eliminates any such effects. For example, the disclosed semiconductor tweezer devices can be configured to have no wires attached to them to minimize the complications of wired interfaces. For example, the disclosed semiconductor tweezer devices can be sterilized (e.g., in an autoclave) so that they can be used on the operating field. For example, the disclosed semiconductor tweezer devices are capable of clamping tissue during a medical procedure by a medical practitioner on a patient. The disclosed devices can be configured as medical instruments and tools that are the same tools that the surgeons are used to using in shape and feel, and yet provide information about the tissue stiffness and size.

In some embodiments, the disclosed semiconductor tweezer device includes a full-body silicon-based structure including: a hinge, legs, arms and microprobes. FIG. 1A shows a diagram of an exemplary silicon-based tweezer device 100 including a hinge structure 101 that is structured to include a spring mechanism, leg components 103 attached to the hinge structure 101 to be held at desired positions relative to each other and movable with respect to each other under the spring mechanism to provide tweezing motion; arm components 105 coupled to the leg components 103, and a microprobe unit 107 that includes a plurality of microscale sensors and/or actuators in one or more sensing tips structured to penetrate into a sample (e.g., biological tissue) when the device 100 clamps the sample. The microscale sensors transduce a mechanical and/or electrical property of the tissue into an electric signal produced by the sensor. The microscale sensors of the microprobe unit 107 can include, but are not limited to, recording electrodes to measure electrical potential of the tissue, electrical permittivity sensors to measure electrical permittivity of the tissue, membrane sensors including piezoelectric resistors on top of a membrane to measure pressure of the tissue based on deformation of the piezoelectric resistors, or strain gauges to measure mechanical compliance of the tissue. The microscale sensors and/or actuators (microprobes) 107 are configured at the end of the leg components 103 away from the hinge structure 101. The arm components 105 are structured to include electronic circuitry, which can include a wireless communications unit including an amplifier, a battery or power source including a self-power source (e.g., solar cell power supply), and wireless transmitters to condition the detected electronic signals from the microprobes 107 and transmit them to a receiver remote from the device 100 (e.g., including transmitting an RF signal to an RF receiver). In some implementations, for example, the electronic circuitry can include a processing unit to process the detected signals from the microprobes 107 and/or the wireless communication unit to transmit the data to a receiver remote. In some implementations, for example, the electronic circuitry can include multiple bonding pads interfacing with another device or circuit, in which the bonding pads are in electrical communication with the microprobes 107 via interconnect wiring on or embedded within the leg components 103. In some embodiments of the device 100, for example, the electronic circuitry can be configured on the leg components 103, e.g., in which the device 100 may or may not include the arm components 105 to provide a surface for a user to grip and tweeze the device 100. The hinge structure 101 can be configured to act as a spring for the tweezing motion. For example, the maximum stress during the tweezing motion can be less than 1 GPa, e.g., to avoid fracturing the exemplary silicon structure. The leg components 103 can be configured to carry electronic signals via electronic interconnection of the sensors of the microprobe unit 107 to the electronic circuitry of the arm components 105.

The leg components 103 can be configured to various lengths, which define the size of the device. In one example, the semiconductor tweezers device 100 can include four 3 mm long microprobes with width of 300 μm and 140 μm thickness, which are placed at the ends of the leg components 103 away from the hinge structure 101. In this exemplary embodiment, polysilicon strain gauges, permittivity sensors, and electrical recording sensors are integrated to form the microprobes 107 of the exemplary multi-sensor full-body silicon tweezers. In an exemplary configuration, four (quad) multi-sensor microprobes are integrated at the end of each leg. The polysilicon strain gauges (e.g., ~15 KΩ), the resistance of which changes with the strain experienced, are connected in an exemplary Wheatstone bridge configuration and integrated at the junction of the leg and the microprobe to measure the longitudinal force and flexural oscillating motion. The permittivity sensor can measure the capacitance at discrete steps under different frequency. The distance coding capacitance can be formed by platinum traces (e.g., 30 μm wide and 0.2 μm thick) co-fabricated on the microprobes. The microprobe structures 107 on the two sides of the tweezer device 100 can also be used to measure distance by measuring the capacitance between the microprobes 107. In some embodiments, for example, 16 platinum recording electrodes can be included, e.g., to provide the capability of biopotential measurement.

In some embodiments, the device 100 can further include a sonic sensor unit 109 to determine the distance between the two leg components 103 during the tweezing motion. In some implementations, for example, two piezoelectric transducers can be configured to transmit sonic pulses at a frequency, for example, of 1-kHz, edge-to-edge of the two legs to measure distance between the two legs, e.g., with 1-5-μm resolution. The pulses can be received on one hand of the leg and filtered with passive LC components and rectified to obtain a received pulse modified in amplitude and time-of-arrival, corresponding to the gap. In some implementations, for example, the piezoelectric traducers, in addition to detecting the distance between the legs components 103 of the tweezer device 100, can also be used in one of its resonance modes to actuate the leg components 103 to move (e.g., oscillate) and cut the tissue. The device 100 can be operated to actuate the tweezer structure to oscillate in longitudinal and/or transverse mode to cut the tissue ultrasonically, which can allow the tweezer device 100 access to stiffer/harden tissue, further expanding the functionality of the tweezer device. For example, the processing unit can provide a control signal to the piezoelectric transducers to actuate the device 100 to cut at least a portion of the sample (e.g., tissue) based on oscillating motion of the piezoelectric transducers operating in one or more resonance modes. Also, for example, the processing unit can provide a control signal to the piezoelectric transducers to actuate the device 100 to oscillate (e.g., longitudinally and/or transversely) by the piezoelectric transducers operating in one or more resonance modes to sonically measure the stiffness of the sample (e.g., tissue).

In some implementations, for example, the exemplary tweezer device 100 can be configured to transmit multiple different RF signals, corresponding to the multiple detected signals, e.g., such as the contact force signal at the strain-gauges, the permittivity signal, the biopotential signals, and the time-of-flight signal from the distance sensor. These RF channels can be recorded in a nearby receiver and on a handheld device. The hand-held device can compute the tissue stiffness from the gripper force signal versus leg-gap. Audio signals that indicate the stiffness, contact with tissue, and over-pressure on tissue can indicate usage status for the surgeon.

In some embodiments, the device 100 can further include an outer support casing that encapsulates at least a portion of the exemplary silicon tweezer structure to provide added structural rigidity and to support the exemplary silicon tweezer structure to remain in plane (e.g., alignment of the microprobes 107 and/or sensor unit 109) over repeated tweezing movements. In some implementations, for example, the outer support casing can encapsulate the hinge structure 101 and a portion of the leg components 103 proximate the hinge structure 101. For example, the outer support casing can be produced using 3D printing techniques.

Tissue Property Measurements

Tissue properties can be measured using different physical modalities, which can be used to differentiate between types of tissues. These include electrical and mechanical characterization at frequencies ranging from DC to microwave. One type of measurement of tissue properties includes electrical admittance. Electrical admittance of the tissue can be difficult to measure in vivo due to physical parameters of measurement tools. From the existing experimental values of conductivity and permittivity, a data model can be used to get parameters from the complex admittance $\sigma_f + j\varepsilon_f = \sigma_\infty + [\Delta\sigma 1 + (jf/f_c)^\alpha]$. These parameters include $\sigma_\infty$ which is the conductivity at very high frequencies, $f_c$ is the characteristic frequency at the apex point of the admittance curve, f is the sample frequency, and $\Delta\sigma$ is the difference in conductivity between the high and low frequencies, while $\alpha$ is a fitting parameter.

Another type of measurement of tissue properties includes probe insertion force. Measurement of insertion force and mechanical modulus can differentiate healthy from unhealthy tissue. Penetration force in tissue can be used to image fine vessels and measure morphology of tissue at 25-50 micron resolution. In an example, a needle with a centimeter-scale force gauge was used to characterize insertion force into prostate tissue, e.g., which was intended to be used in robotic brachytherapy where a needle is inserted in the tissue, and force-torque data is collected, where exemplary results show that cancer tissue is harder, prostate density and PSA have significant effects on mean forces. Some previous measurements of the prostate visco-elastic properties indicated the Young's modulus of normal tissue is 15.9±5.9 kPa, while cancerous tissue is 40.4±15.7 kPa. Examples of sensors in devices that can penetrate into tissue in 1D are described in U.S. Pat. No. 8,197,418 entitled "MICROPROBES", which is incorporated by reference in its entirety as part of the disclosure of this patent document.

Another type of measurement of tissue properties includes resonance properties. Previous studies have shown that resonance properties of piezoelectrically driven actuators in tissue have significantly different resonance frequencies, and loss-factors, and the viscosity of cancer tissue is higher than normal tissue.

Medical practitioners, e.g., such as surgeons, make decisions on the use of different instrumentation that provide a spectrum of information on living tissue. For example, surgeons use various tools providing contact forces to decide if, where, and how to cut and manipulate tissue. These decisions are mostly made without quantitative data about the mechanical integrity and mechanical properties of the tissue.

Given that different approaches can be used to characterize tissue, as described above, it would be beneficial to the medical practitioners to have a device such as the disclosed semiconductor tweezers that can measure the various properties during medical treatment (e.g., surgery) with minimal effect on the time or procedure protocol.

The disclosed semiconductor tweezer devices can be used to determine electromechanical properties of tissue tweezed by the device. In some implementations, the disclosed semiconductor tweezer devices can be utilized by medical practitioners for characterizing living tissue of patients, e.g., such as before and during surgical procedures. In some embodiments, for example, the semiconductor tweezer device can include an integrated silicon-based design of the backbone structure and microsensors, actuators and electronic circuits. For example, this silicon tweezer device can exhibit a spring constant of 9 N/m, and maximum silicon stress of 80.7 MPa during the tweezing motion to prevent silicon fracture. In an exemplary embodiment, multiple thin-film sensors can be integrated along with the silicon tweezer, four sets of strain gauges, two sets of permittivity sensors and sixteen platinum bio-potential recording electrodes. Therefore, insertion force, permittivity and electrical properties of tissue can be monitored simultaneously at different locations provide fast information in time critical surgeries. A set of piezoelectric transducers can be attached on the legs of the tweezer for gap monitoring, e.g., with 20 μm displacement resolution in some implementations. The tissue stiffness can then be determined by the measured through applied force and distance variation. These exemplary semiconductor tweezer devices can be used to resolve a key problem during intestinal anastomoses surgical operations, e.g., where stapling devices are used to seal tissue. The semiconductor disclosed tweezer devices provide a platform for clinical use during medical diagnosis and treatment procedures such as surgery.

Exemplary Device Architecture

Figure 1B:
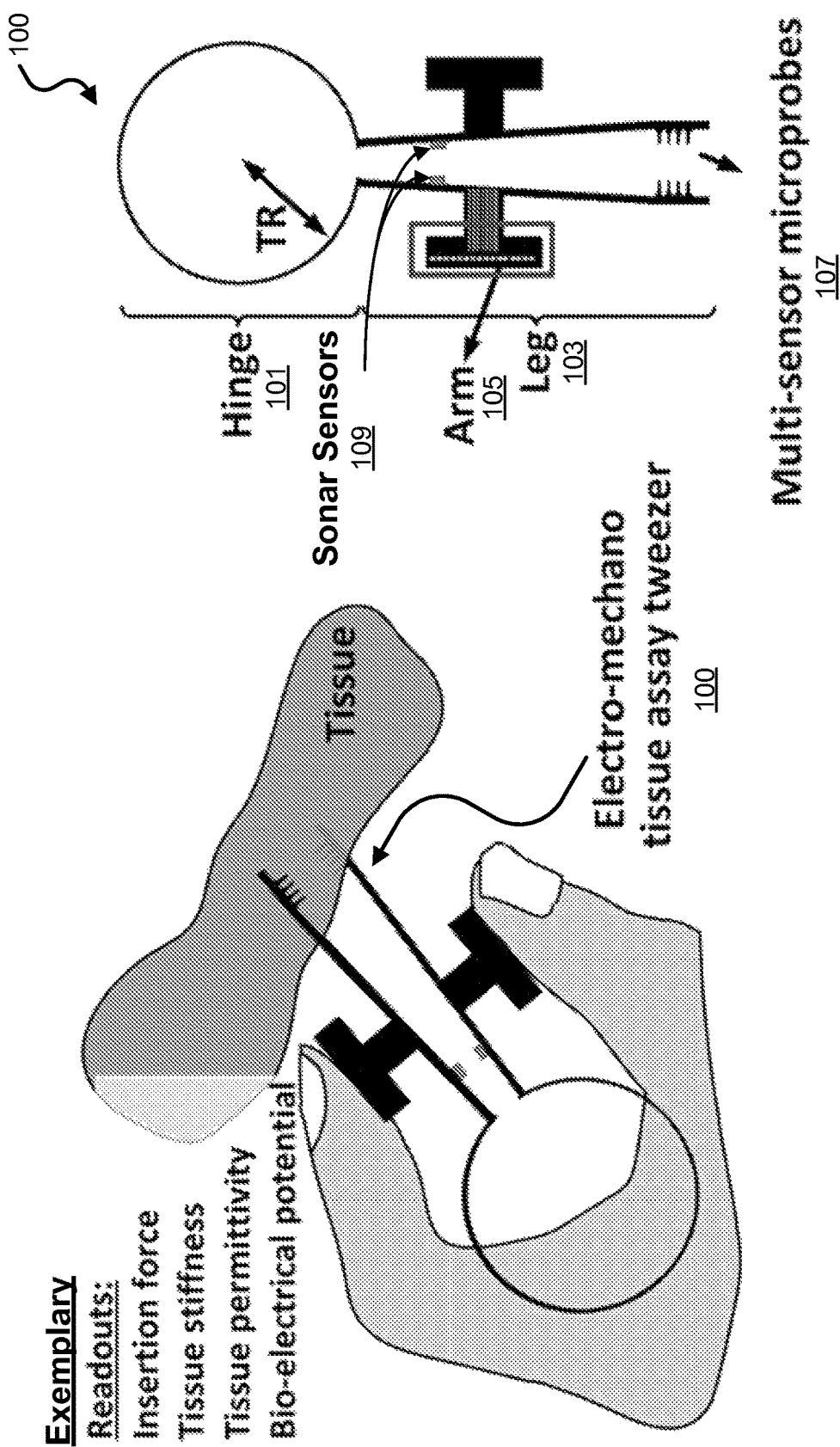

FIG. 1B shows another diagram of the exemplary silicon-based tweezer device 100 for characterizing electromechanical properties of tissue. The device 100 includes an all-silicon tweezer design that enables repeatable tissue assessment across medical procedures without external calibration. The exemplary all-silicon tweezer device 100 can be fabricated using lithographic techniques with the precision of a few microns (e.g., over a 10-cm tweezer device size), and can provide ~1-10 part-per-million repeatability of spring constants and force sensitivity. The exemplary all-silicon structure also enables extensive embedded sensor integration, e.g., alongside CMOS circuits, for a highly functional medical tweezer. The exemplary all-silicon design of the device 100 integrates permittivity and strain gauge sensors, and thereby provides an exemplary tool-set on a single device that can revolutionize the choice of the anastomotic technique and technology used. The device 100 can provide multiple tissue property measurements of various tissue characteristics, for example, including but not limited to compliance, electrical potential, and permittivity, which better inform the medical practitioner at the time of the medical procedure. For example, the device 100 can provide quantitative data that can be analyzed by a processing unit on board the device 100, or remotely on a remote computing device or devices, e.g., such as a handheld computing device (e.g., smartphone, tablet, laptop, or wearable computing device), a desktop computer, or computers in a communication network (e.g., servers in the cloud). The quantitative data can be analyzed by the processing unit to determine the tissue thickness, the tissue stiffness, the tissue permittivity, and/or bioelectrical potential of the tissue. Such information can be used to determine whether a medical device tool, e.g., such as a surgical stapler, is suitable for a medical procedure such as an intestinal anastomosis, which this information can be presented to the medical practitioner in real-time during the measurement using the device 100.

In an illustrative example, the measurement of tissue stiffness and thickness provided by the silicon-based tweezer device 100 can enable a surgeon to make the proper determination of the tissue suturing technique during a surgery. By knowing if the tissue is too stiff or too thick, hand suturing maybe warranted. Within the appropriate tissue thickness, the measurement will indicate what size staples are needed for optimum tissue apposition and healing. These live measurements can help the surgeon to make better tissue-suturing decisions and reduce the 1-7% postoperative dehiscence rate. The reduction of the dehiscence rate has the potential to spare thousands of patients this catastrophic complication, save millions of dollars to healthcare and reduce the cost of medical malpractice to hospitals and physicians, surgery safer and saving lives, while providing higher confidence during training for younger inexperienced surgeons.

FIG. 1B shows an illustrative schematic of the exemplary silicon-based electro-mechano tissue assay tweezer device 100. As shown in the right portion of the illustrative schematic, the device 100 includes the hinge 101, the arm components 105, the leg components 103, and the microprobes 107. The hinge 101 includes a structural and material design capable of tweezing movement without exceeding silicon maximum fracture stress. In the exemplary schematic of FIG. 1B, the two arm components 105 include several bonding pads for interfacing with a PC-board via interconnect wiring from the leg components 103 to the microprobes 107. Alternatively or additionally, the arm components 105 can include built in electronic circuitry including a data processing unit and communications unit. For example, the data processing unit can include a processor to process data and a memory unit in communication with the processor to store data. For example, the processor can include a central processing unit (CPU) or a microcontroller unit (MCU). For example, the memory unit can include processor-executable code, which when executed by the processor, configures the data processing unit to perform various operations, such as receiving information, commands, and/or data, processing information and data, and/or transmitting or providing information/data to another device via the communications unit. The memory unit can store the signal data detected from the microprobes 107 (e.g., converted to digital format by an analog-to-digital converter), as well as other information and data, such as instructions, software, values, images, and other data processed or referenced by the processor. Various types of Random Access Memory (RAM), Read Only Memory (ROM), Flash Memory, and other suitable storage media can be used to implement storage functions of the memory unit. The data processing unit can include an I/O unit that can be connected to the communications unit or an external interface, source of data storage, or display device. Various types of wired or wireless interfaces compatible with typical data communication standards can be used in communications of the data processing unit with other devices, e.g., including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces.

As shown in FIGS. 1A and 1B, the hinge structure 101 is a deformable loop shaped structure with an opening where the leg components 103 are attached to the terminal ends of the opening of the loop shaped hinge structure 101. The loop shaped hinge structure 101 provides the spring mechanism to allow the loop to deform under force and to restore its shape so that an operator can use fingers to squeeze the two leg components 103 to use their tips to clamp and hold a tissue or an object and to release the squeezing to let go the tissue or object. This is further illustrated in FIG. 1C and FIG. 7 below. In other implementations, the hinge 101 can be in other configurations to provide similar tweezing operations as shown in FIGS. 1A, 1B, 1C and 7.

Figure 1C:
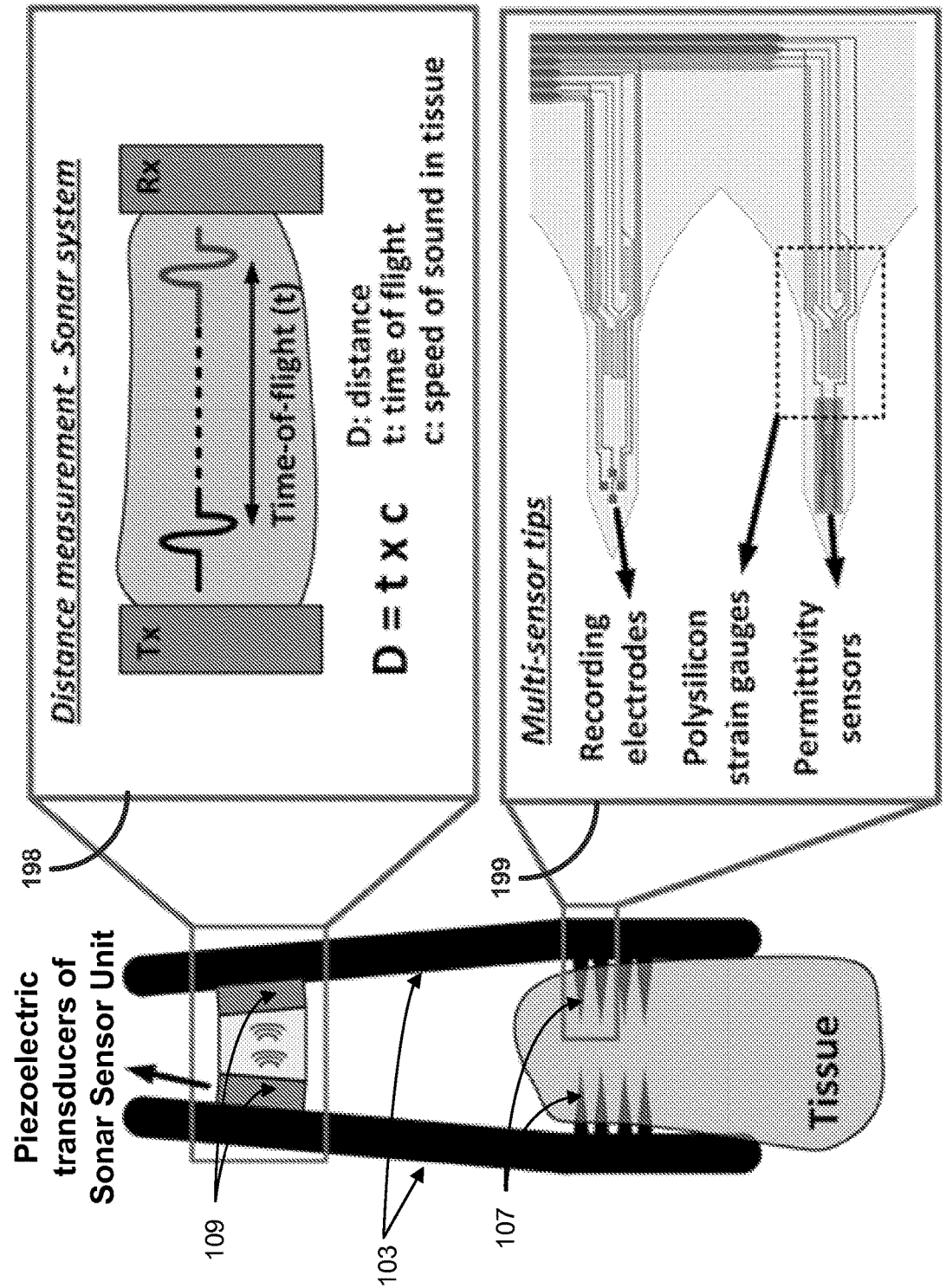

FIG. 1C shows an illustrative schematic of the exemplary silicon-based electro-mechano tissue assay tweezer device 100 grasping tissue where the microprobes unit 107 is inserted into tissue during the tweezing motion for measuring different tissue properties, e.g., such as, compliance, electrical potential and permittivity. The insert box 198 of FIG. 1C shows an illustration depicting the distance measurement by the sonar sensor between the two probe leg components 103, e.g., which can be measured through the time of flight signal transmitted and received from the piezoelectric transducers with known speed of sound in tissue. The insert box 199 of FIG. 1C shows an illustration depicting the tissue stiffness based on signals detected by the multi-sensor tip microprobes, e.g., and which can be calculated from the distance variation versus the force variation. Tissue permittivity properties can also be monitored. As shown in the insert box 199, the multi-sensor tip microprobes 107 featured in this example include recording electrodes and polysilicon strain gauges in one microprobe tip (top tip of insert box 199), and permittivity sensors and polysilicon strain gauges in another microprobe tip (bottom tip of insert box 199), in which these microsensors are electrically coupled to the electronic circuit of the arm components 105 via interconnect wires.

Figure 1D:
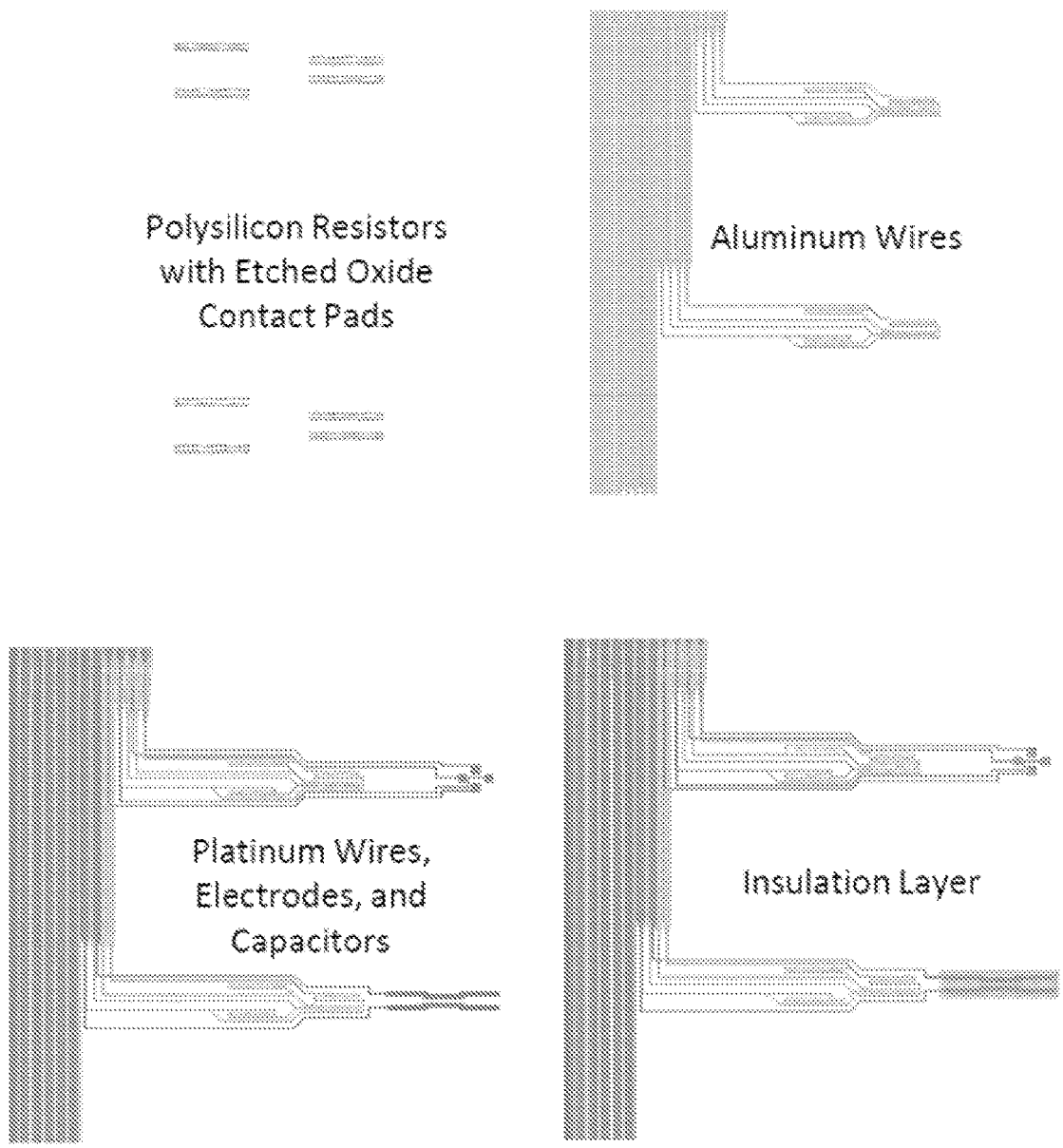
FIG. 1D shows an exploded diagram of an exemplary embodiment of the microprobes of the exemplary semiconductor tweezer device of FIG. 1C.

FIG. 1D shows an exploded diagram of an exemplary embodiment of the microprobes 107 of the exemplary semiconductor tweezer device 100 depicted in the insert box 199 of FIG. 1C. The multi-sensor tip microprobes 107 can include polysilicon resistors with etched oxide contact pads that are electrically coupled to the electronic circuit via interconnect wires (e.g., which can be aluminum interconnect wires, as shown in the top right feature of FIG. 1D). The multi-sensor tip microprobes 107 can include electrode structures and capacitors to at least partially form the recording electrodes and permittivity sensors shown in FIG. 1C, which are electrically coupled to the electronic circuit via interconnect wires (e.g., which can be platinum interconnect wires, as shown in the top right feature of FIG. 1D). The multi-sensor tip microprobes 107 can include electrical insulator features to at least partially form the recording electrodes and permittivity sensors shown in FIG. 1C.

Figure 2A:
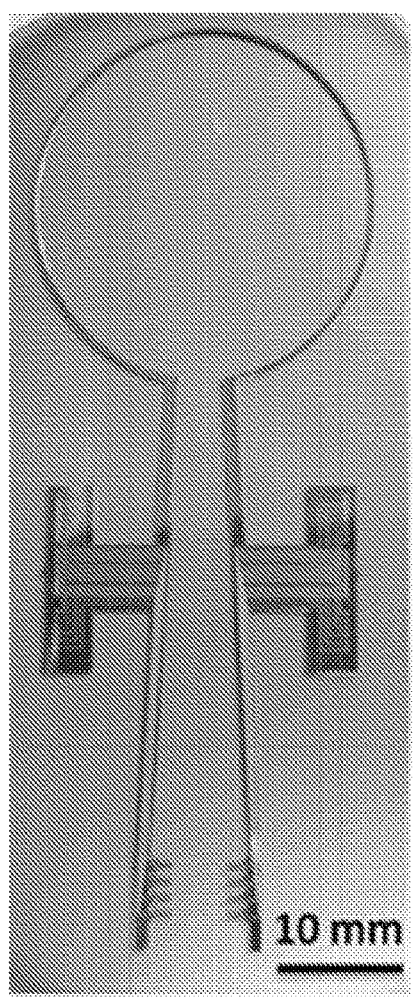
FIGS. 2A-2C show photographic images of exemplary fabricated silicon-based tweezer devices.
Figures 2B, 2C:
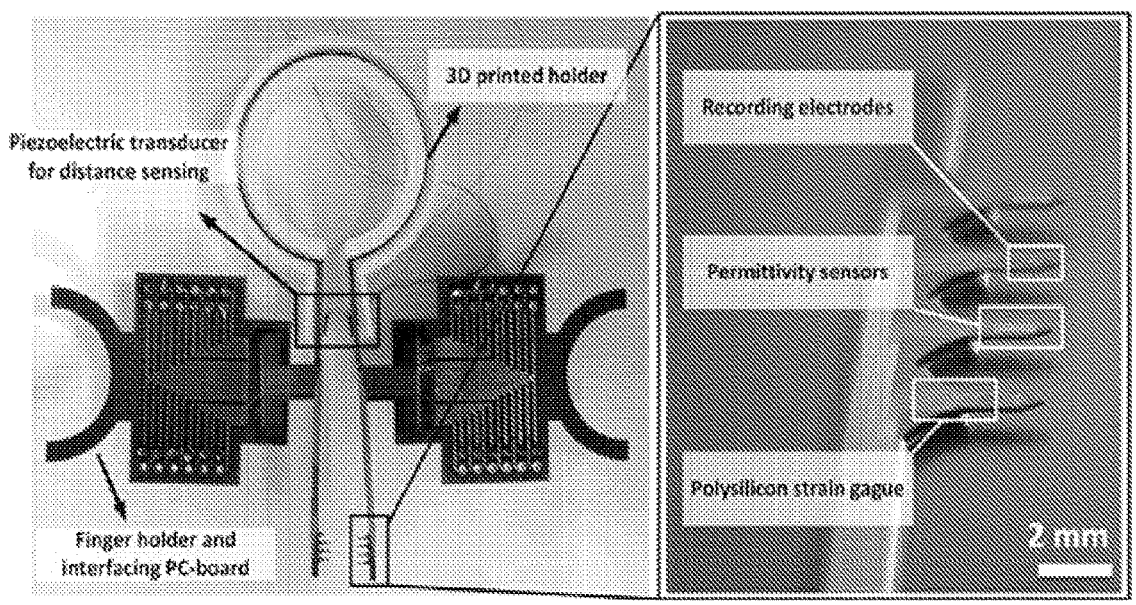

FIGS. 2A-2C show photographic images of exemplary fabricated silicon-based tweezer devices. FIG. 2A shows an optical image of an exemplary silicon-based tweezer device including the plurality of bonding pads for electronic interfacing with a computing device (e.g., via a PC board). FIG. 2B shows an optical image of an exemplary silicon-based tweezer device including a hinge holder component that encapsulates the hinge structure 101 of the device, a finger-holder section of the arm component 105, and the piezoelectric transducers of the sonar sensor for distance sensing of the device. The microscale multi-sensor probes of the exemplary devices shown in FIGS. 2A and 2B are shown in a magnified optical image in FIG. 2C.

Exemplary Implementations

The device 100 can be implemented to characterize the elastic properties of tissue, in which applied force and deformation is measured simultaneously. For example, force can be measured using the integrated strain gauge of the microprobes unit 107, and distance of deformation can be measured using a pair of ultrasonic transducer sensors of the sonar sensor 109.

Figure 3A:
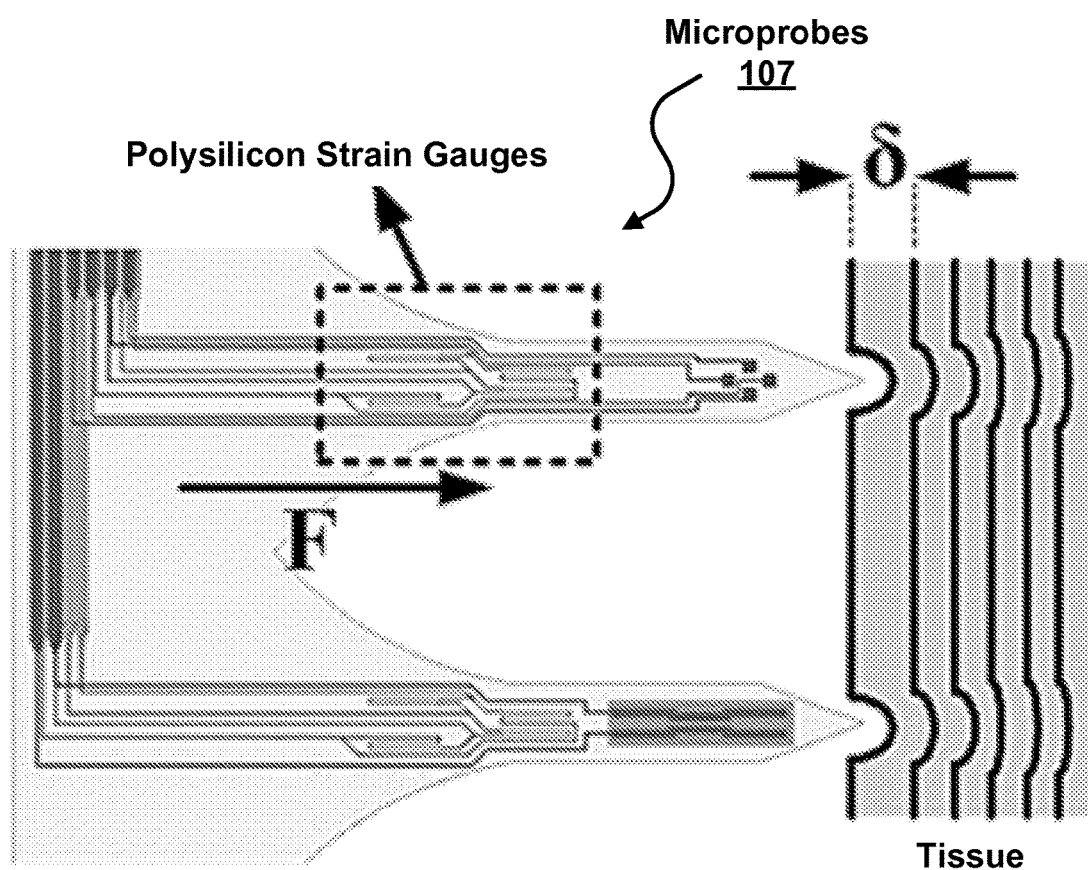
FIG. 3A shows an illustrative diagram depicting soft tissue deformation during tweezing motion of an exemplary semiconductor tweezer device.

For force measurements using the exemplary device 100, the microprobes of the microprobe unit 107 will indent tissue longitudinally during tweezing motion, as depicted in FIG. 3A. FIG. 3A shows an illustrative diagram depicting soft tissue deformation caused by the microprobes 107 during tweezing motion of the exemplary device 100. The force versus displacement relationship for a rigid indenter can be estimated in Equation (1) as:

$$F = \frac{2}{\pi} \tan\alpha \frac{E_{tissue}}{1-v^2} \delta^2 \qquad \text{Eq. (1)}$$

where $E_{tissue}$ is the tissue Young's modulus, $\delta$ is the displacement, $v$ is the Poisson's ratio, $\alpha$ is the half angle opening in the indentation. The Young's modulus of various tissues are shown in Table 1.

In an illustrative example for force measurements of muscle, the Young's modulus is ~8 kPa, the Poisson ratio of soft tissue is ~0.5, and assuming half angle opening is 15 degree, and assuming the displacement is 10% of the 1 centimeter tissue thickness, then the force can be estimated as ~1.19 mN. The strain from the strain gauge on the exemplary silicon microprobe can then be calculated as $1.68 \times 10^{-7}$. The voltage obtained from the polysilicon strain gauge with gauge factor of 20 and 5 V applied voltage ($V_{applied}$) can be estimated as 16.8 µV. With amplification, this signal is sufficient for tissue characterization with high signal to noise ratio.

TABLE 1

Young's modulus of different soft tissues.

| Tissue | Average Young's modulus (kPa) |
|---|---|
| Liver | ~950 |
| Arteriovenous | ~3600 |
| Breast tissue | ~8 |
| Muscle | ~7 |
| Spinal cord | ~3 |

For distance measurements using the exemplary device 100, a Time-of-Flight (TOF) based system is used for measuring the distance between the exemplary silicon tweezer leg components 103. In some implementations of the device 100, for example, two PZT transducers of the sonar sensor unit 109 are placed on the leg component 103, e.g., with 2% of gelatin gel as acoustic impedance matching layer in between. A 20 MHz pulse can be emitted from one of the transducers of the sonar sensor unit 109 (e.g., through the gelatin gel) and picked up by the other transducer on the other leg component. The distance between the exemplary silicon tweezer leg components 103, referred to as D, can be estimated by the time delay ($T_f$) between the pulse emission and receiving as $D=C \times T_f$, where C is the propagation velocity of acoustic in the medium. In some implementations, for example, measured distance resolution may be limited by the signal-to-noise ratio (SNR) and bandwidth of the receive amplifier to capture the received wave.

Exemplary Simulation of an Exemplary Silicon Tweezer Device

Figure 3B:
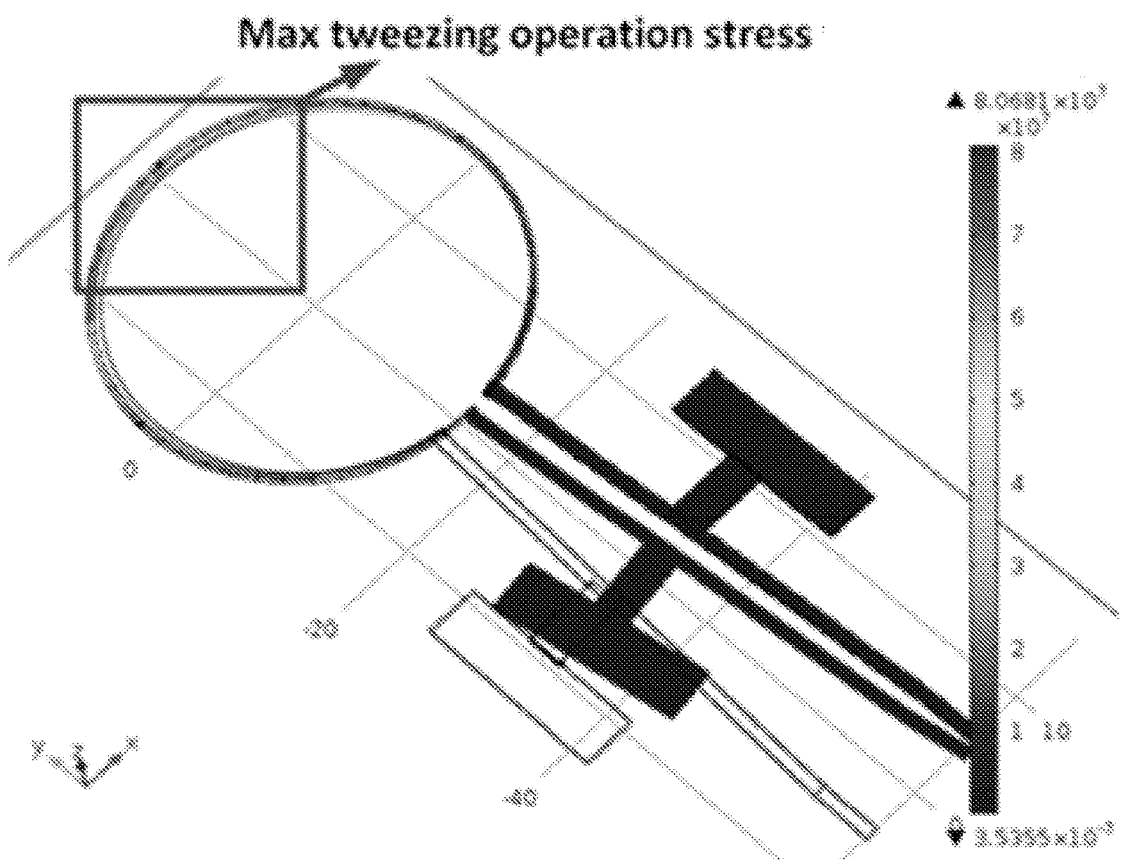
FIG. 3B shows a diagram of the exemplary COMSOL simulation depicting location of maximum stress on an exemplary silicon tweezer device during tweezing movement.

An all-silicon tweezer device was designed with the hinge structure 101, leg components 103, arm components 105, and microprobes 107 as previously described. In this example, the hinge structure 101 included the following design parameters. The silicon tweezing radius-of-curvature (TR=Turn Radius) was designed for taking less than the maximum silicon stress of 1-3 GPa to avoid silicon fracture. An exemplary COMSOL simulation showed that, with a tweezer structure having a 8000 µm hinge radius, 40000 µm leg length, and 1 cm in inter-probe distance, the highest stress point is at the top of the circular hinge and it has a maximum stress of 80.7 MPa. FIG. 3B shows a diagram of the exemplary COMSOL simulation indicating that the maximum stress occurred at the top of the hinge during the tweezing movement.

Also, in this example, the leg components 103 carried interconnects from the microprobes 107 to the clamping-arm 105 for electronic interfaces. Also, the exemplary all-silicon tweezer device in this example included two piezoelectric PZT transducers (e.g., 1.7×3.5×0 5 mm) as part of a sonar sensor unit that were adhesively attached on the leg components 103 near the arm components 105 to measure the distance between the leg components 103 transmitting sonic pulses, e.g., at a frequency of 20-MHz, edge-to-edge of the two legs, to measure distance between the two leg components 103, e.g., with 15 µm resolutions. The pulses were received on one hand of the leg component and filtered with passive LC components and rectified to obtain a received pulse modified in amplitude and time-of-arrival, corresponding to the gap.

Also, in this example, the microprobes 107 were designed to have a quad microprobe configuration and be 3-mm long with 300 µm width and 140 µm thick multi-sensor microprobes. The quad microprobes were integrated at the end of each leg component 103 to provide measurements along the tissue length. Exemplary simultaneous measurements of tissue stiffness at different points provided fast measurement of stiffness gradients, e.g., which is advantageous and/or necessary in time critical medical procedures, such as surgeries. The exemplary polysilicon strain gauges of the microprobes unit 107 used in this example were integrated at the junction of the leg component 103 and the microprobe unit 107 to measure the longitudinal and flexural strain due to tissue contact. The exemplary permittivity sensor was implemented by measuring capacitance versus frequency across two electrodes. A total of sixteen platinum recording electrodes were also co-fabricated in this exemplary all-silicon tweezers device design to provide the capability of bio-potential measurement.

Exemplary Results of Implementations Using the Exemplary Silicon Tweezer Device

Spring Constant Measurements:

Exemplary implementations of the exemplary all silicon tweezer device were performed. The exemplary implementations included a simulation to estimate the spring constant of the tweezer structure given the parameters above. For example, it was found that with one side of the tweezers fixed and the other allowed some degrees of freedom for movement, the spring constant was around 2 N/m. For the exemplary implementation, the tweezers were moved from 0 to 3500 µm in increments of 500 µm over 5 trials using a motorized micromanipulator. It was found that the spring constant was 9 N/m, which is higher than the exemplary COMSOL simulation because it accounts for the friction of the platform that the tweezers are placed on. The exemplary platform itself was built using a 3D Printer.

Figure 4A:
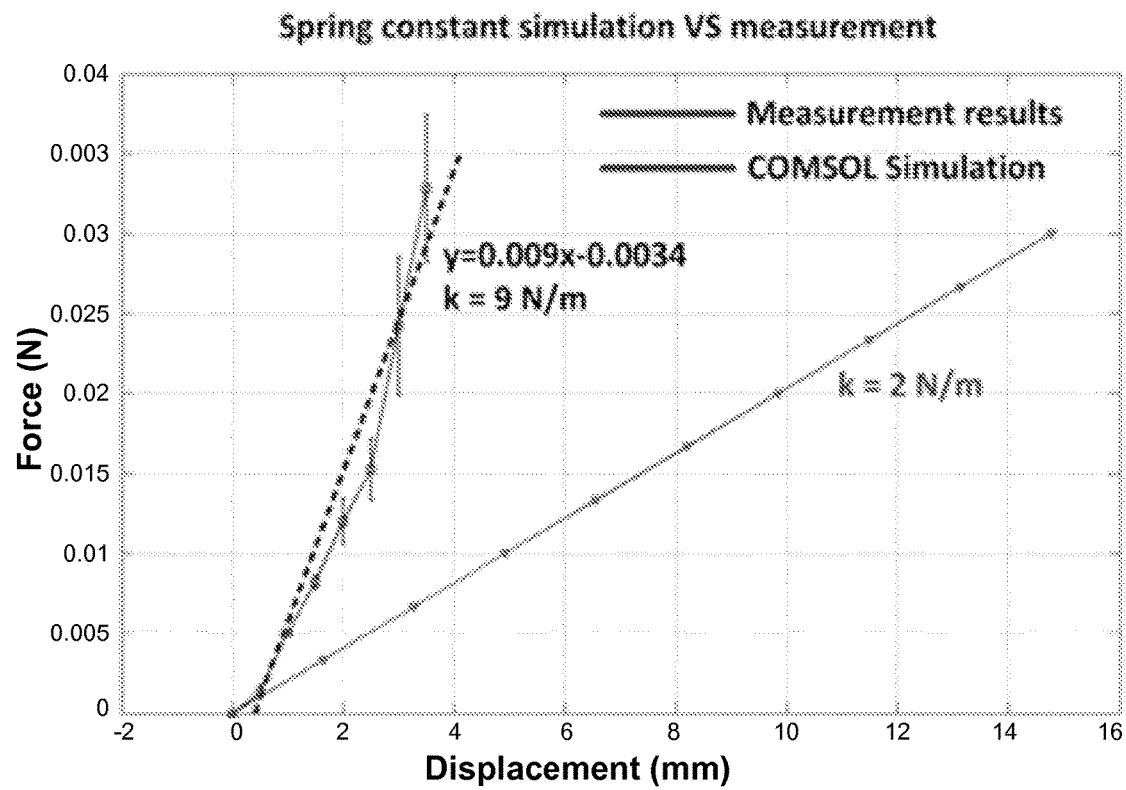
FIGS. 4A and 4B show data plots depicting the measured spring constant of an exemplary silicon tweezer device.

The exemplary implementations included analysis of the feasibility of the probes' strain gauges for measuring insertion force and tissue elasticity. FIG. 4A shows a data plot showing the measured spring constant of the exemplary silicon based tweezer structure. For example, a measurement environment was set up to parameterize insertion speed into gelatin samples; the sample in this case was 0.01 oz. to 10 mL of water. Four probes on one side of the tweezers were detached from the completed structure and were placed 8608 µm vertically above the gelatin sample. In all of the exemplary implementations described, the probes were attached to a 4-channel differential amplifier set at a gain of 200. This amplifier was then connected to a NI-DAQ USB and the data was transferred to LabView. Taking the resulting data, running it through a 5th Butterworth Low-Pass Butterworth filter, the exemplary results were obtained.

Figure 4B:
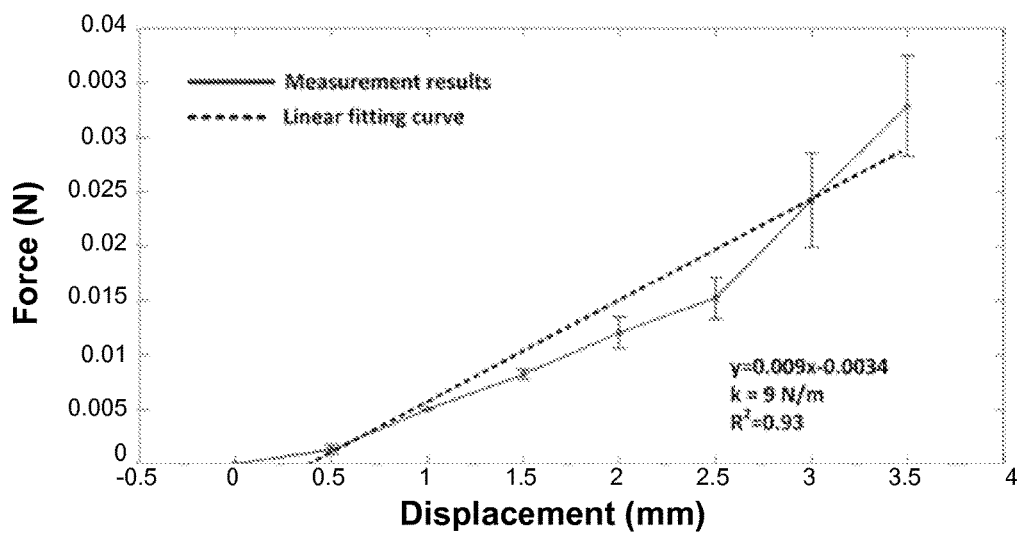

FIG. 4B shows a data plot depicting the exemplary measurement and simulation values of the spring constant of the exemplary all silicon tweezer device. The exemplary tweezer spring constant was measured with a commercial force gauge with one arm fixed. The exemplary measurement results yielded a spring constant of 9 N/m, e.g., which is sufficient for human tweezing motion.

Integrated Stain Gauge Signal Measurements:

The exemplary implementations included characterization of insertion speed control of the microprobes of the exemplary silicon tweezer device. Insertion forces for two types of gelatin samples under various insertion speeds were monitored through the integrated stain gauge. In this example, four probes of the microprobe unit 107 were inserted into the gelatin mixtures at varying speeds. The voltage difference before and after insertion with different gelatin samples under different speed were measured. Overall, for example, the insertion force increases with insertion speed by 15% for every 1000 μm/s increase in speed, as shown in FIGS. 5A-5E. It is noted, for example, that the gelatin concentration from 9% to 18% decreases the insertion force by an average of 28%, as shown in FIG. 5B.

Figure 5A:
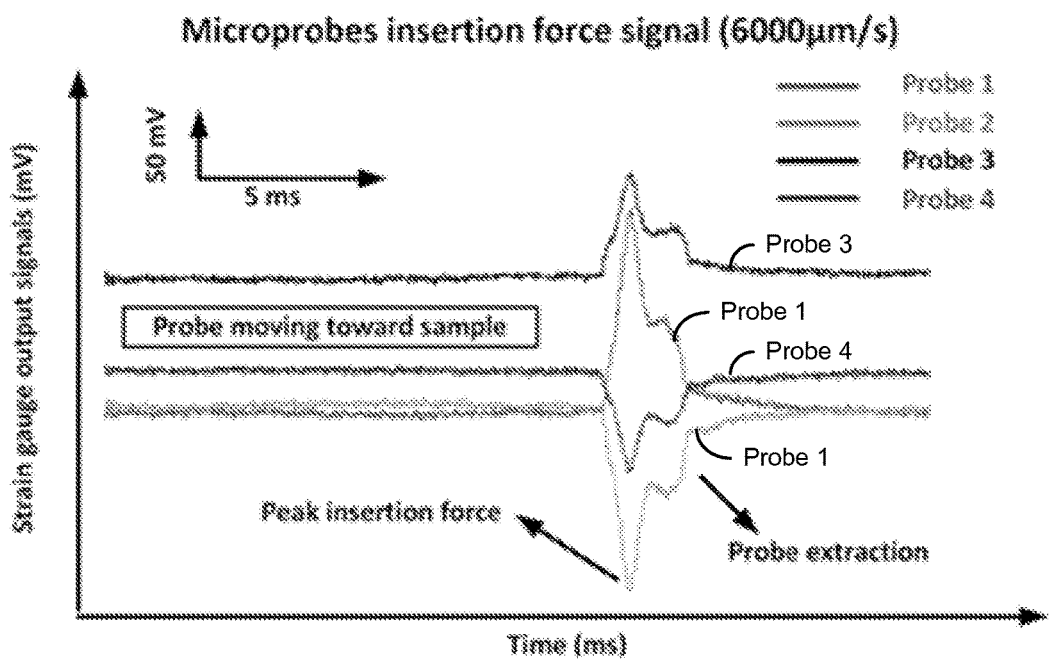
FIGS. 5A-5E shows data plots depicting insertion control speed of the microprobes of the exemplary silicon tweezer device inserted in a sample at various speeds.
Figure 5B:
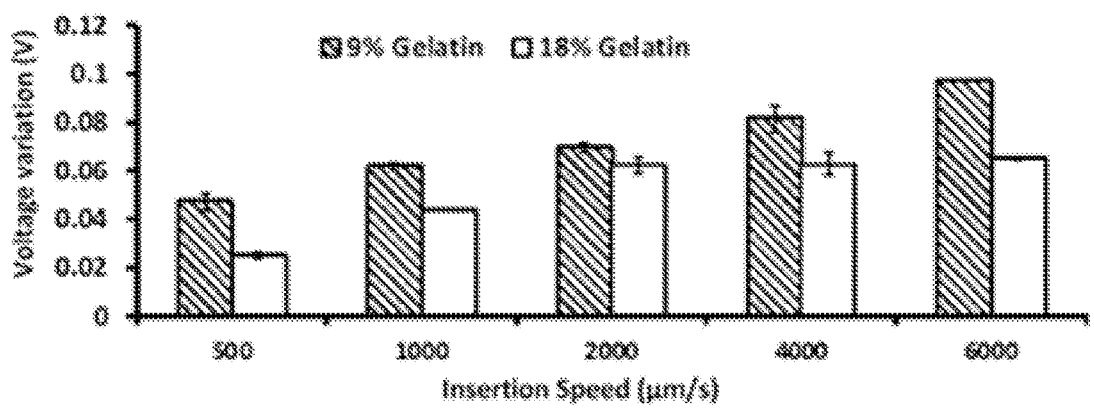

FIG. 5A shows a data plot depicting the microprobes insertion force signal for an exemplary insertion speed analysis at 6000 μm/s and at a height of 8608 μm above the exemplary gelatin sample. For example, at the point of insertion, the probe values obtained from this exemplary implementation were (1) 130 mV, (2) 124 my, (3) 68 mV, and (4) 66 mV.

The exemplary attached device can also be used with only one half of the exemplary tweezer, such that the devices can be used lateral implant probes. For example, a distribution of sensors such as strain-gauges and electrical pads can be used to measure electrical impedance of tissue along with distributed stiffness to help characterize tissue and perhaps identify tissue, e.g., such as cancer.

FIG. 5B show a data plot of the measured strain gauge signals depicting voltage variations of two different percentage of gelatin gel under different insertion speeds.

Figure 5C:
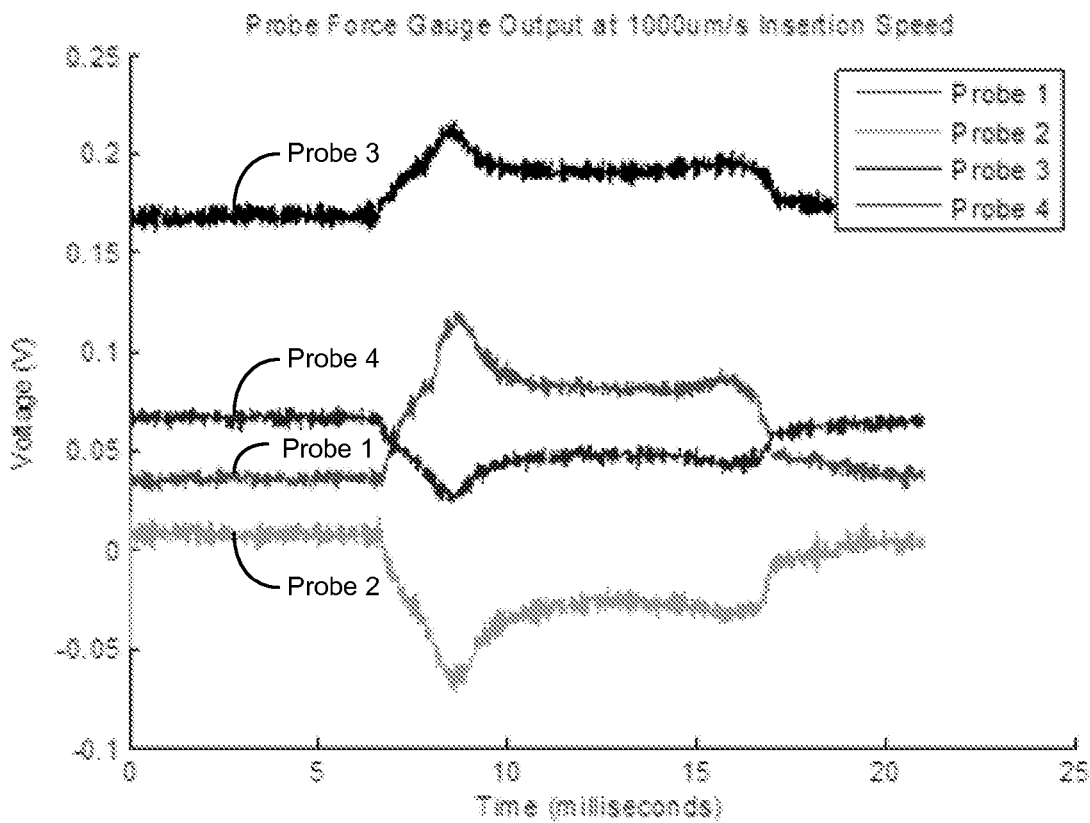

When the vertical insertion speed was decreased to 3000 μm/s, the new voltage changes from the probes were (1) 125 mV, (2) 108.5 mV, (3) 71 mV, and (4) 62.6 mV. The exemplary results are displayed in FIG. 5C. FIG. 5C shows a data plot showing an exemplary insertion speed analysis at 3000 μm/s at a height of 8608 μm above sample.

Figure 5D:
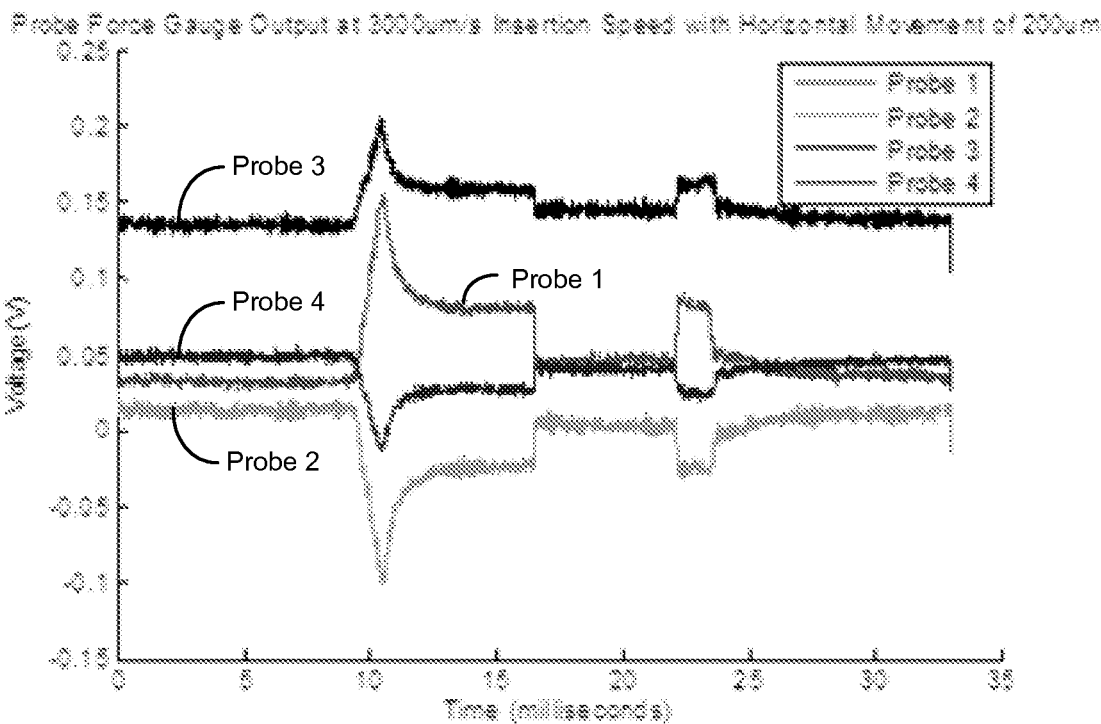

Similarly when the vertical insertion speed was decreased to 1000 μm/s, the new voltage changes were (1) 83.8 mV, (2) 83.5 mV, (3) 4.75 mV, and (4) 4.34 mV. The exemplary results are shown in FIG. 5D. FIG. 5D shows a data plot showing an exemplary insertion speed analysis at 1000 μm/s at a height of 8608 μm above sample.

Figure 5E:
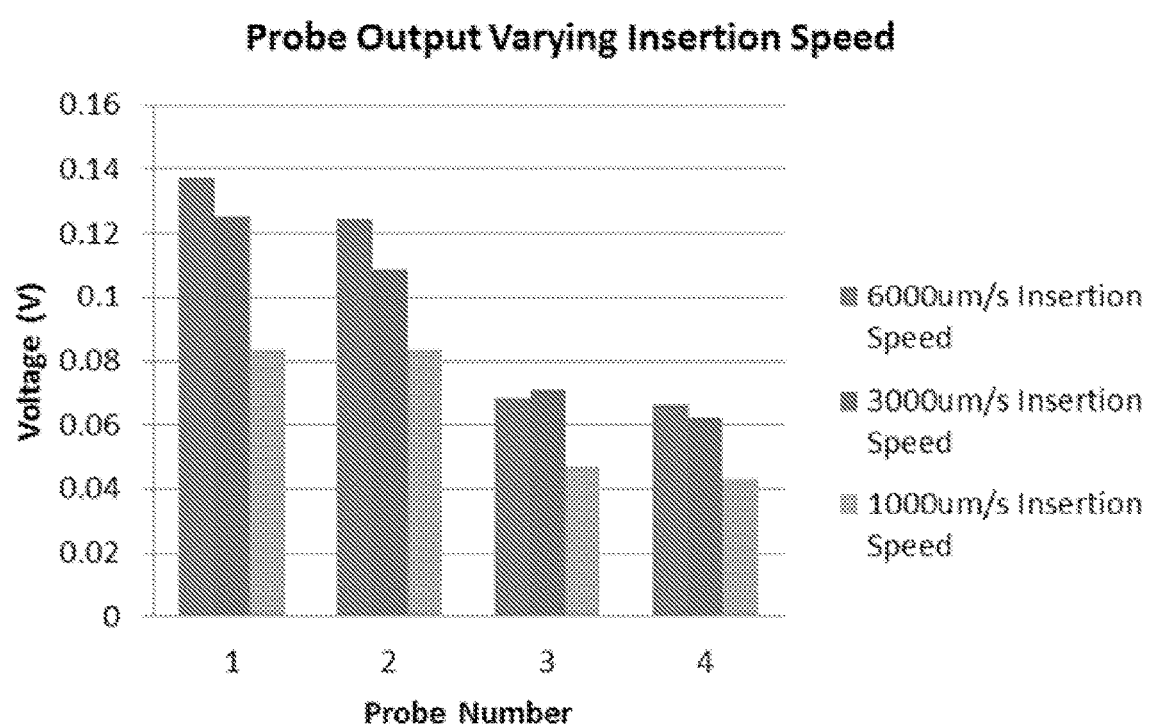

FIG. 5E shows a data plot showing an exemplary insertion speed data analysis. Exemplary results from the insertion speed tests show that as the insertion speed decreases, the voltage change also decreases.

Figure 6A:
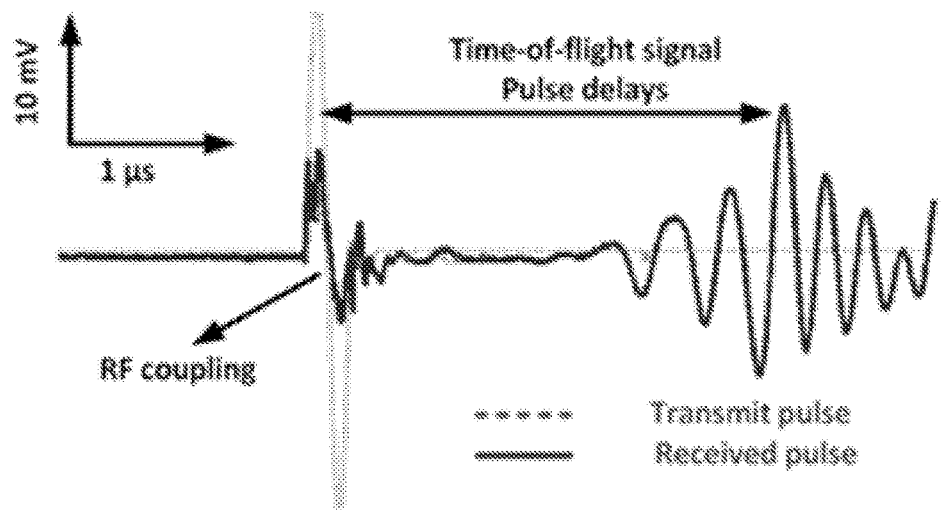
FIGS. 6A and 6B show data plots depicting the time of flight measurements recorded between the highest amplitude of emission and receiving pulses.
Figure 6B:
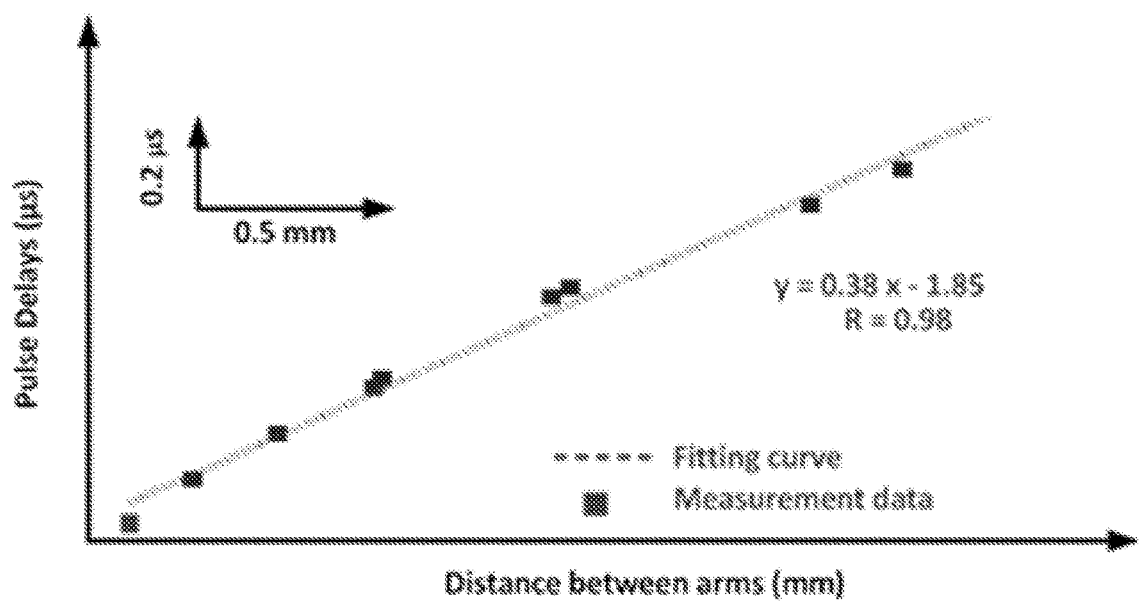

Distance Measurements:

The tweezer speed and gap versus time was monitored by the exemplary sonar sensor unit 109 of the exemplary silicon tweezer device, in which PZT pulse-echo displacement versus time measurements were performed using the exemplary device, as shown in FIGS. 6A and 6B. The distance between two probe legs can be measured through the time of flight signal transmitted and received from the piezoelectric transducers with known speed of sound in tissue. FIGS. 6A and 6B show data plots depicting the time of flight measurements recorded between the highest amplitude of emission and receiving pulses. FIG. 6A shows a data plot of the piezoelectric transducer time-of-flight signal measurement. FIG. 6B shows a data plot of the characterization of pulse delays over different distances between the two leg components.

As shown by the exemplary implementations of the silicon tweezer device, the disclosed multi-functional semiconductor devices and instrumentation can characterize electromechanical properties of tissue. The exemplary silicon tweezer structure was shown to undergo tweezing motion without silicon fracture and to have a spring constant characterized as 9 N/m, for example. The gap during tweezing motion can be monitored by a sonic sensor unit, e.g., including a set of piezoelectric transducer, attached on the leg components using pulse-echo displacement measurements over time.

In another aspect of the disclosed technology, the microscale sensors, actuators circuitry of the disclosed semiconductor tweezer devices can be configured to integrate and fit within existing medical instruments and tools (e.g., surgical tools). For example, in some implementations, a 3D printed structure having the structural form of a medical instrument (e.g., such as a surgical tool, like a surgical tweezers) can be created with cavities for such microsensors, actuators and electronics of the disclosed technology to be integrated.

Figure 7:
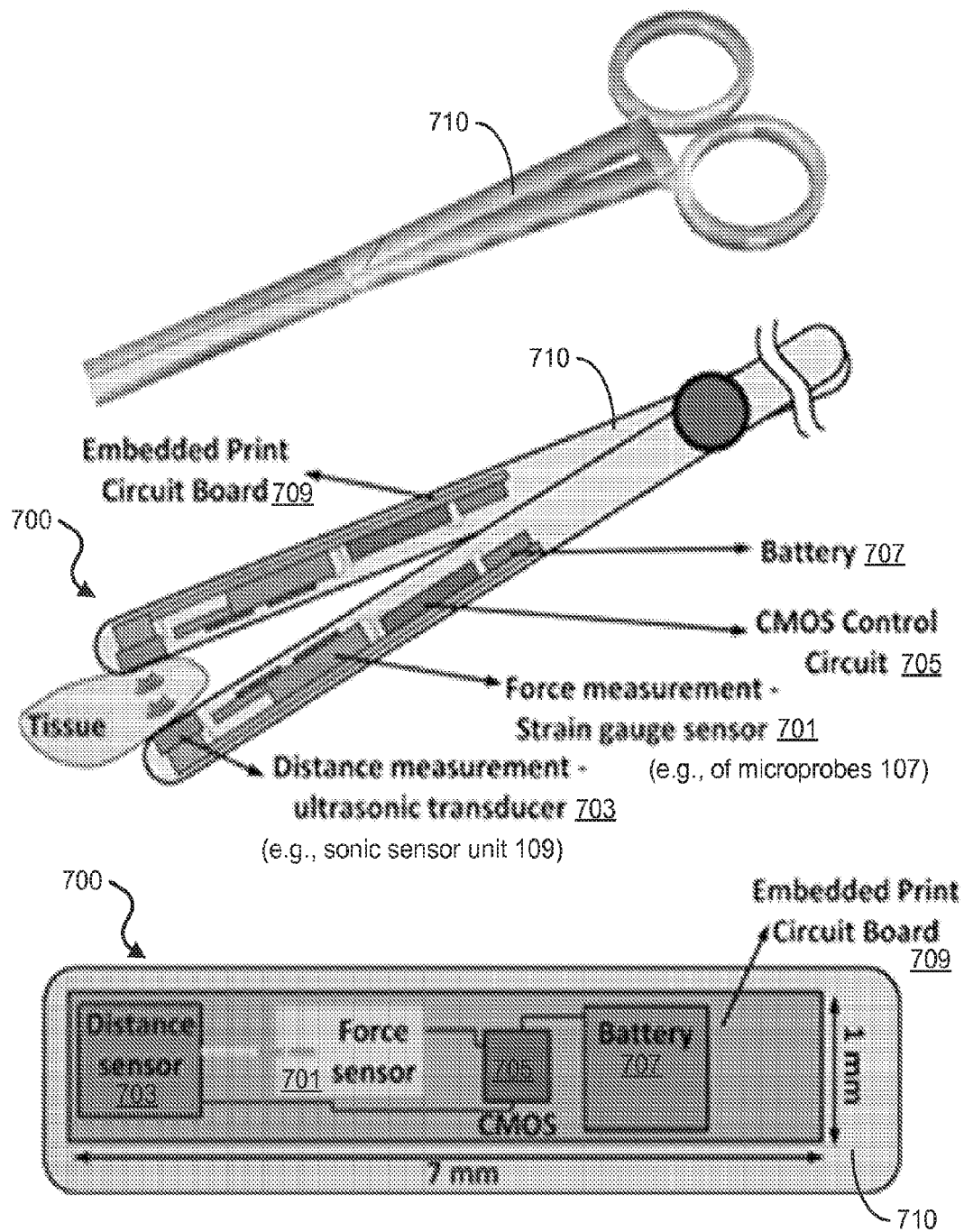
FIG. 7 shows a diagram of an exemplary caliper device including microsensors, actuators, and electronics of the disclosed technology.

In one exemplary embodiment, a medical device can include a configuration of the microprobes unit and the processing and/or communication unit configured for implementations in a caliper format (e.g., 'grippers'). FIG. 7 shows a diagram of an intelligent medical device 700 that integrates an exemplary strain gauge probe 701, ultrasonic transducer distance sensor 703, a control unit 705 (e.g., CMOS control circuit including RF transceiver), and a power supply 707 (e.g., battery, such as a solar cell power unit) on a printed circuit board 709, which are embedded on each side of an exemplary caliper structure 710. For example, the solar cell power unit can be integrated into a center region of the device for self-power, e.g., such as by fabricating a large area of P/N junction co-fabricated with the semiconductor tweezer components of the device 700. The solar cell power unit can harvest energy for powering the components of the device 700 (and/or the device 100), e.g., such as the sensors 701 and/or 703 and the control unit 705, by converting from the high intensity light of an operational room, for example. In some implementations, for example, semiconductor junctions formed in the tweezer structure can serve to convert light from the outer environment of the device 700 (or the device 100) to generate electricity for powering the sensors 701 and/or 703 and the control unit 705.

In some implementations, the exemplary device 700 of FIG. 7 can be configured on a 1 mm×7 mm flex printed circuit board (PCB) with at least some of exemplary components of the device 100, e.g., including strain gauges of the microprobes unit 107, sonic transducers of the sensing unit 109, and an RF transceiver, battery (e.g., solar power battery), and/or a processing unit of the electronics of the arm component 105. For example, the strain gauge can be embedded in a plastic (PPSF) compound via molding or by placing in a 3D printed PPSF part, which can be autoclaved. As the two sides of the gripper squeeze on a tissue, the strain gauges can measure the gripper-hand flexure corresponding to the normal force applied to the tissue. At the same time, for example, two 100-MHz piezoelectric transducers can be transmitting sonic pulses at a frequency, for example, of 1-kHz, edge-to-edge of the two grippers to measure distance between the two gripper hands, e.g., with 1-5-μm resolution. The pulses can be received on one hand of the gripper and filtered with passive LC components and rectified to obtain a received pulse modified in amplitude and time-of-arrival, corresponding to the gap. The intelligent medical gripper device can transmit multiple different RF signals, corresponding to the multiple detected signals, e.g., such as the contact force signal at the strain-gauges, and the time-of-flight signal from the distance sensor, as well as other signals detected from the tissue using other sensors incorporated in the integrated semiconductor tweezer structure of the device 700 (e.g., such as the permittivity signal from an electrical permittivity sensor, and/or the biopotential signals from recording electrodes). For example, the control unit 705 can include an analog-to-digital converter to convert the electrical signals detected by the sensors 701 and/or 703 from analog to digital format, in which the digital signals are transmitted, e.g., on multiple channels as the different RF signals. The transmitted RF signals can be recorded in a nearby receiver and on a handheld device. The hand-held device can compute the tissue stiffness from the gripper force signal versus gripper-gap. Audio signals that indicate the stiffness, contact with tissue, and over-pressure on tissue can indicate usage status for the surgeon.

Figure 8:
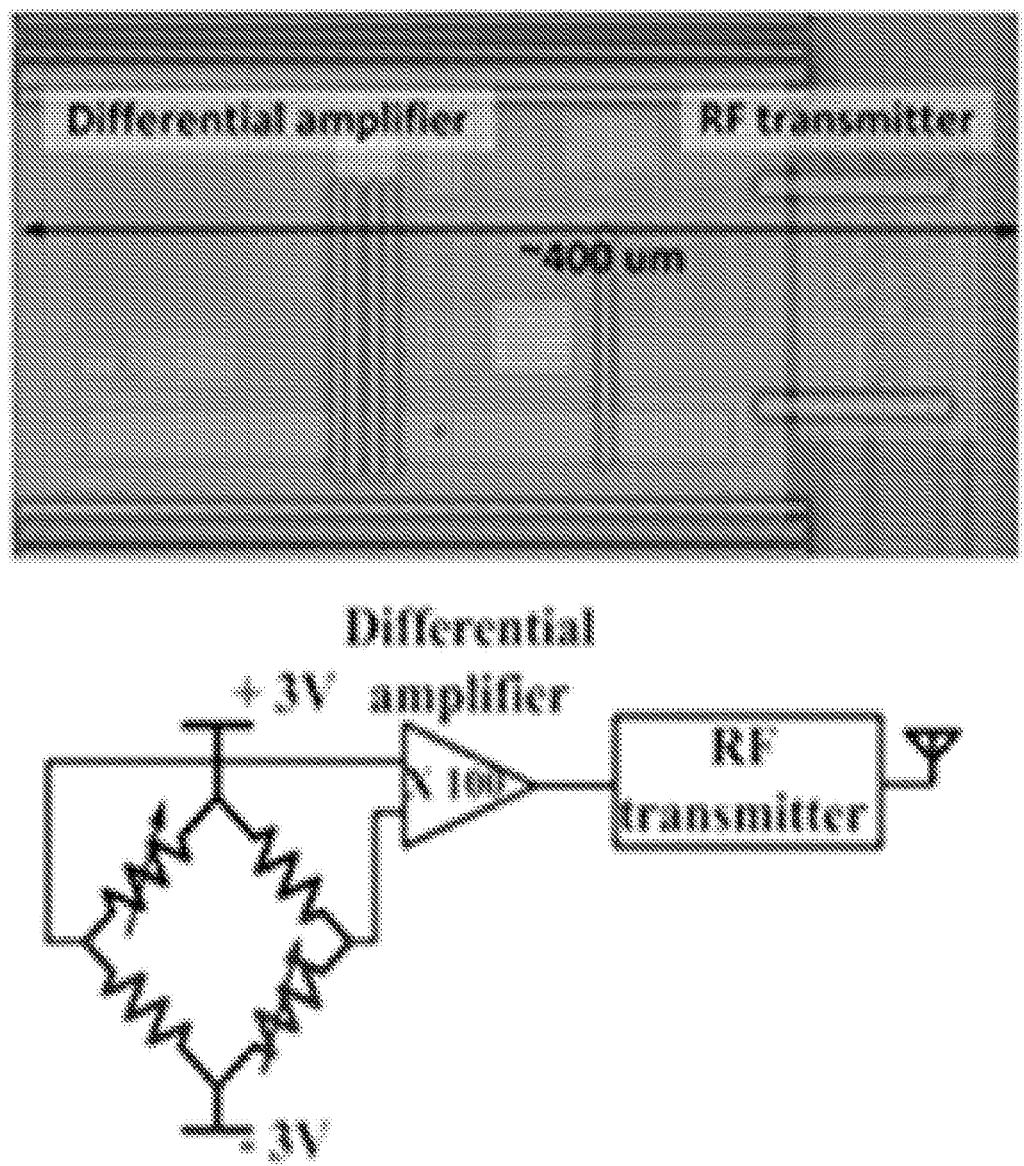
FIG. 8 shows a diagram of an exemplary integrated circuit with an amplifier and RF transceiver for wireless data communication.

FIG. 8 shows a diagram of an exemplary integrated circuit with an amplifier and RF transceiver to transmit (and/or receive) data wirelessly. The amplifier and transceiver system shown in FIG. 8 can be included in the exemplary silicon tweezer device 100 shown in FIGS. 1A-1C, for example, to process the signals from the different sensors and actuators of the microprobes 107 and/or sonic sensor 109, e.g., strain-gauges, electrical signals, piezoelectric transducers, etc. Similarly, the amplifier and transceiver system can be included in the control unit 705 of the device 700 and integrated with the micro electro-mechano components in the grippers shown in FIG. 7. This front-end system can amplify signals from sensors through an instrumental amplifier and transmit by a RF modulator. In some examples, a miniaturization front-end system can be implemented by a customized integrated circuit and biased at ±1.5 V, e.g., same bias as the exemplary strain gauge of the exemplary microprobes 107. Such a system can be miniaturized as an ASIC such that it can be bonded and connected to the disclosed tweezer devices. An exemplary embodiment of an ASIC system is shown in FIG. 8, e.g., in 180 nm CMOS which includes preamplifiers, power supply shifters, and oscillators that use on-chip and off-chip inductors. This exemplary system can be implemented to transmit strain signals from a multi-probe-based system. Hence each tweezer device can transmit different RF signals, the contact force at the strain-gauges and the time-of-flight signal from the distance sensor. These RF channels can be recorded in a nearby receiver and on a handheld device.

In another aspect, the disclosed technology includes fabrication processes to produce the microprobes of the disclosed semiconductor tweezer devices. In one embodiment, for example, a method to fabricate the microprobes 107 of an exemplary silicon based tweezer device, e.g., such as of the device 100 or of the device 700, includes a process to produce one or more polysilicon strain gauge resistors by implementing a low pressure chemical vapor deposition (LPCVD) technique in which polysilicon is implanted with boron, e.g., at a dose of $2 \times 10^{15}$ ions/cm$^2$ at 100 keV, over a silicon nitride layer formed on a silicon substrate. The method includes a process to produce one or more resistors that are electrically contacted with aluminum alloy (e.g., Al+1% silicon) metal lines. The method includes a process to produce an insulation layer over the resistor and strain gauge structures formed on the substrate by depositing a nitride deposition layer using a plasma-enhanced chemical vapor deposition (PECVD) technique. The method includes a process to define the electrical recording sites and produce the permittivity sensors by implementing chromium and/or platinum evaporation over the nitride layer and lift off to form the desired geometry of the chromium and/or platinum layers. The method includes a process to produce another insulation layer over the exposed nitride layer and chromium and/or platinum layers formed on the substrate by depositing a second nitride deposition layer using PECVD technique. The method includes a process to etch the fabricated layered structure to produce (i) etched regions for contact wire connections to the resistors (e.g., aluminum layer) and/or permittivity sensors (e.g., platinum layer), and (ii) etched regions on the front-side and back-side of the fabricated layered structure to produce the strain gauge structure. For back-side etching, a polymer coating (e.g., Protek SR-25) can be spun to protect the front-side features during deep reactive ion etching (DRIE) technique for probe release.

Figure 9:
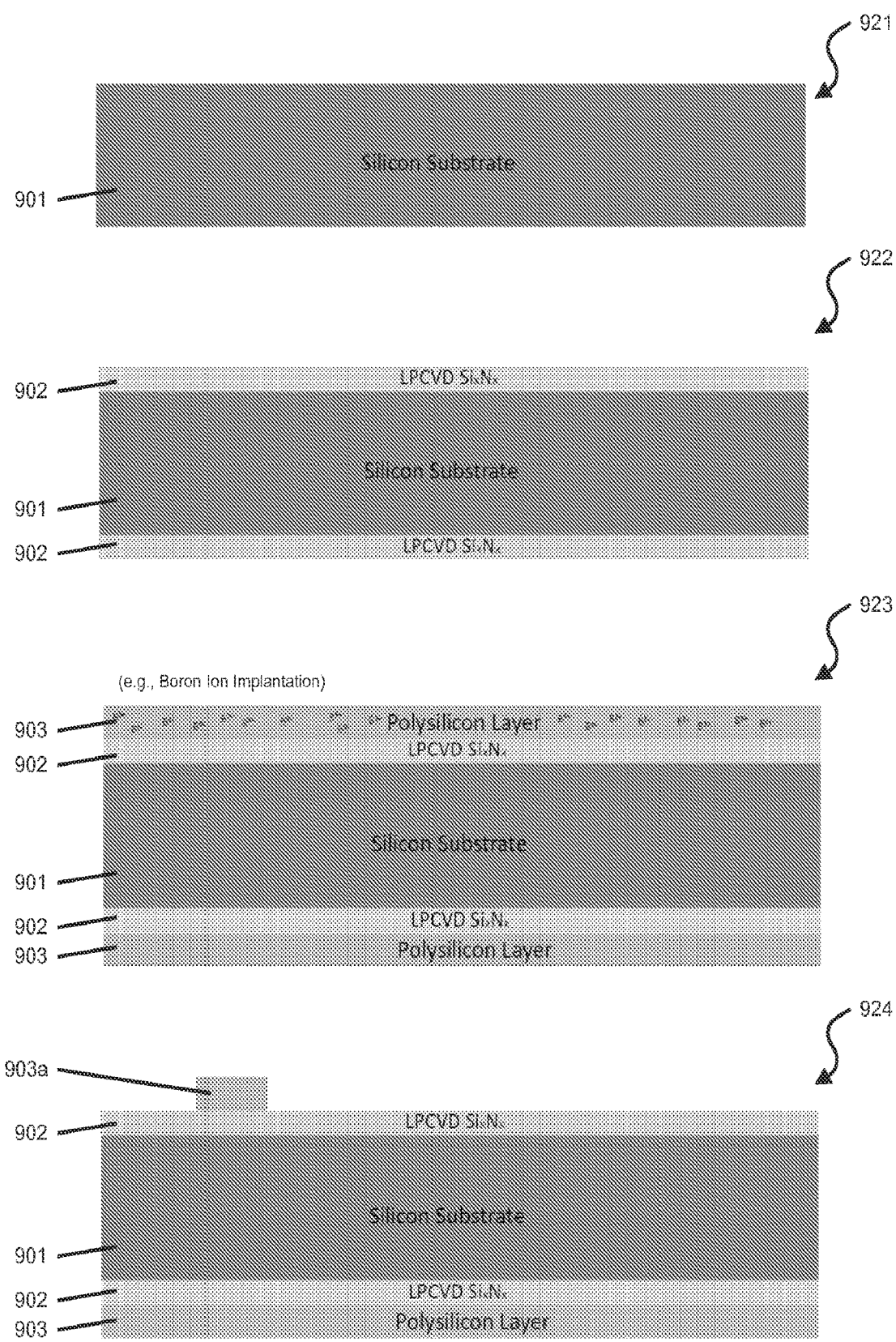
FIG. 9 shows an illustrative diagram of an exemplary fabrication method to produce the integrated silicon the microprobe structure of the exemplary silicon tweezer devices.
Figure 9:
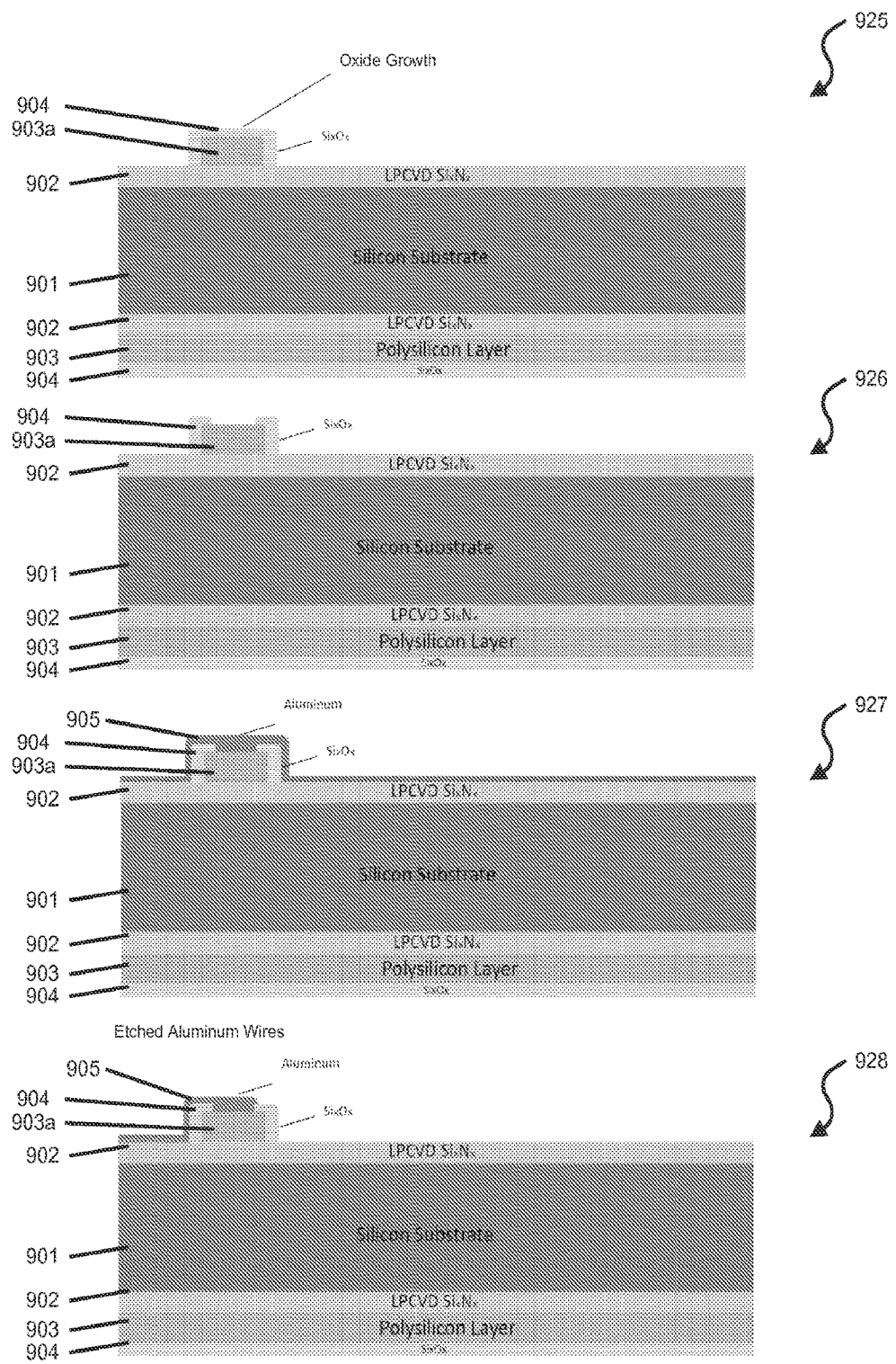
Figure 9:
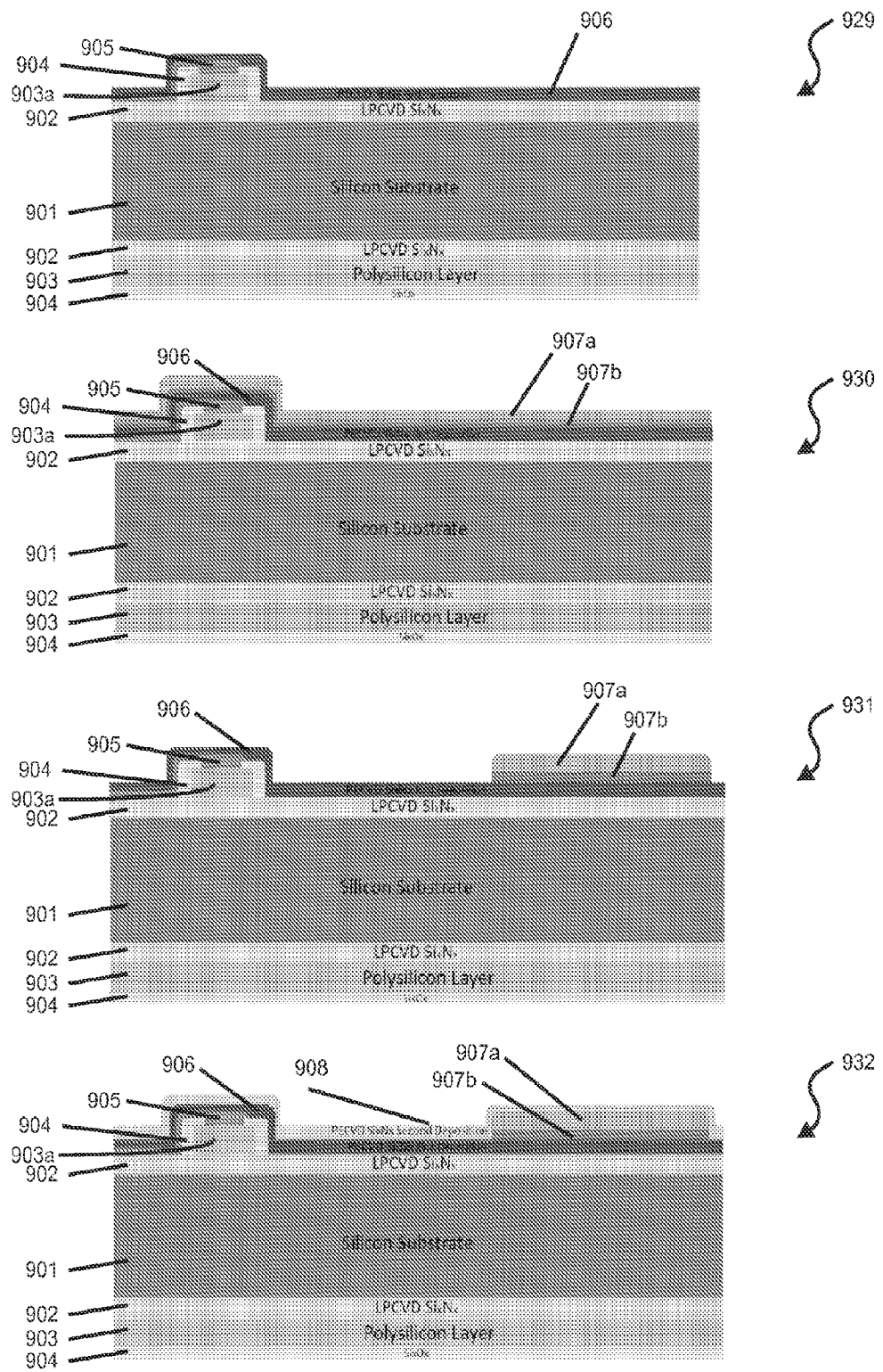
Figure 9:
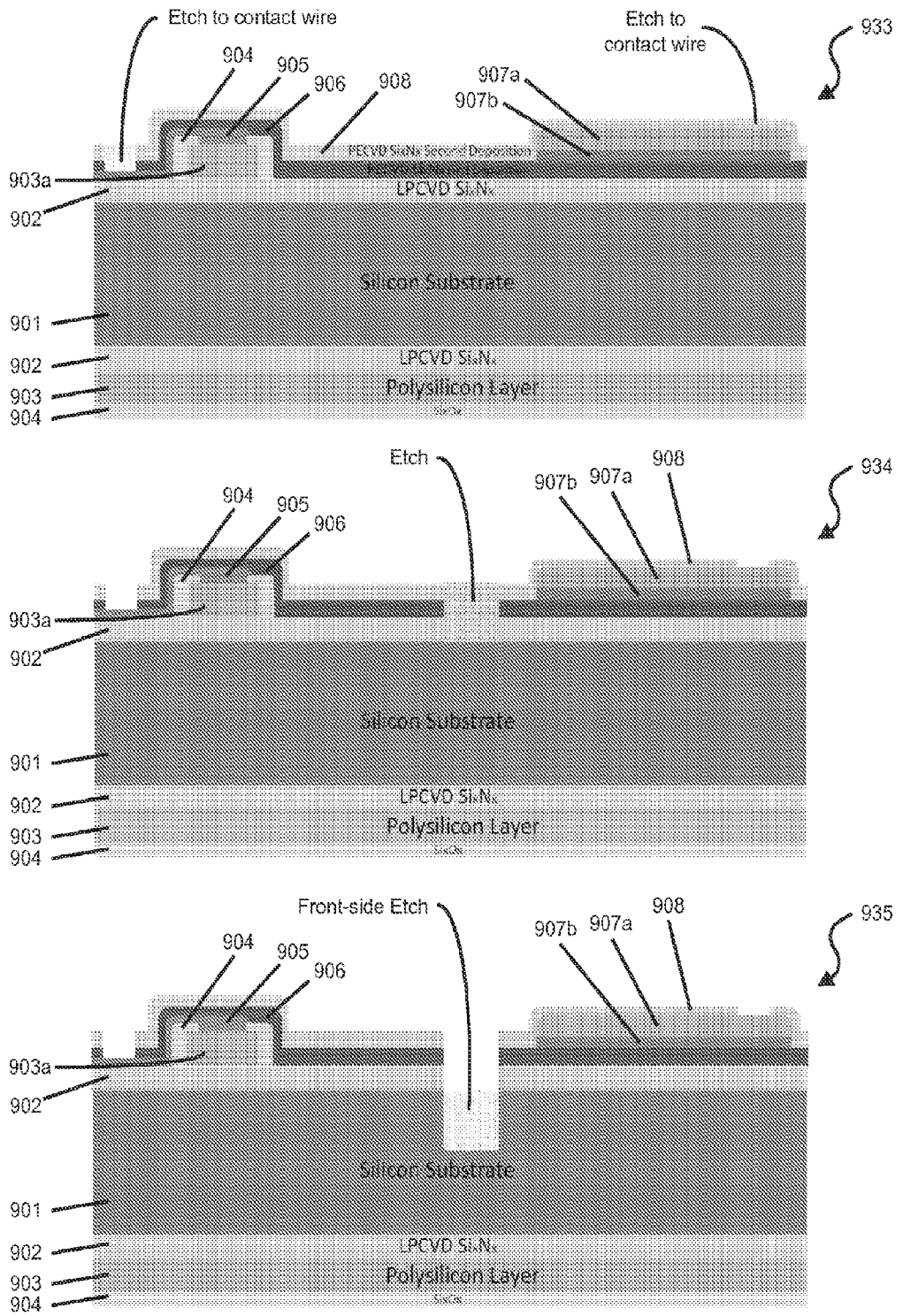
Figure 9:
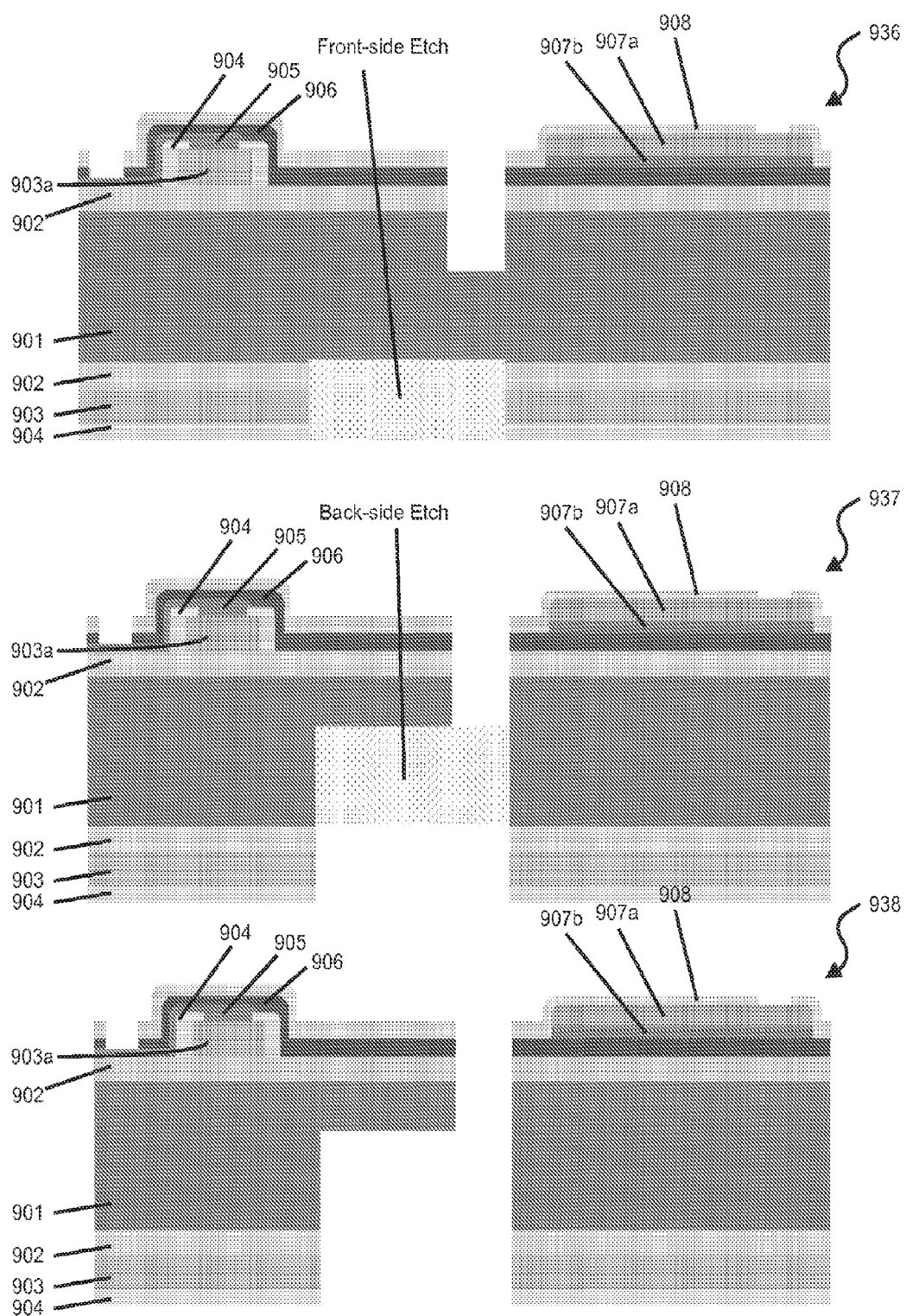

FIG. 9 shows an illustrative diagram of an exemplary fabrication method to produce the integrated silicon component structure of disclosed silicon tweezer devices. The method includes a process 921 to provide a semiconductor substrate 901 (e.g., silicon substrate). The method includes a process 922 to deposit a substrate insulator layer 902 (e.g., LPCVD silicon nitride, e.g., approximately 600 nm thick) using LPCVD on both sides of the substrate 901. The method includes a process 923 to deposit a polysilicon layer 903 (e.g., approximately 600 nm thick) and implant boron ions in the polysilicon layer 903. In some implementations of the process 923, for example, annealing may be performed for better ion distribution and to relieve the stress of the polysilicon layer 903. The method includes a process 924 to etch the polysilicon layer 903 on one side (e.g., the front side) to form a resistor pattern 903a of the polysilicon. The method includes a process 925 to grow an oxide layer 904 (e.g., approximately 300 nm thick of silicon oxide $Si_xO_x$) from the polysilicon layer 903 and polysilicon resistor pattern 903a, and thereby forming a multi-layered structure. The method includes a process 926 to etch a portion of the oxide layer 904 over the resistor pattern 903a to form a contact site to connect a wire (e.g., an electrically conductive interconnect). The method includes a process 927 to form a layer of an electrically conductive material 905, e.g., such as aluminum by sputter coating the aluminum, over the front side of the multi-layered structure to cover the substrate insulator layer 902 and the etched oxide layer 904 covering the resistor pattern 903a of the polysilicon. The method includes a process 928 to etch the conductive layer 905 over a selected region of the multi-layered structure to form a wire structure of the electrically conductive material 905 (e.g., aluminum wire). The method includes a process 929 to deposit a first insulative material 906 (e.g., LPCVD silicon nitride, e.g., approximately 600 nm thick) using LPCVD on the front side of the multi-layered structure. The method includes a process 930 to form a metal layer 907 (e.g., which can include one or more metals, such as a layer of chromium 907a approximately 200 Å thick, and a layer of platinum 907b approximately 2200 Å thick over the layer 907a) by evaporation techniques over the first insulative material 906. The method includes a process 931 to remove portion of the metal layer 907 (e.g., 907b and 907a) by lift-off process to form an island of the metal structure 907. The method includes a process 932 to deposit a second insulative material 908 (e.g., LPCVD silicon nitride, e.g., approximately 1000 nm thick) using LPCVD on the front side of the multi-layered structure. The method includes a process 933 to etch a portion of the insulative layers 906 and 908 to form contact sites with the electrically conductive material 905 (e.g., aluminum wire) and the metal structure 907. The method includes a process 934 to etch a region of the insulative layers 906 and 908 and the substrate insulator layer 902 on the front side, e.g., exposing the substrate 901 in the etched region. The method includes a process 935 to etch a portion of the substrate 901 (e.g., approximately 200 nm) in the etched region from the process 934, e.g., by DRIE technique. The method includes a process 936 to etch a region of the oxide layer 904, the polysilicon layer 903, and the substrate insulator layer 902 on the back side, e.g., exposing the substrate 901 in that etched region (e.g., approximately 200 nm). The method includes a process 937 to etch a portion of the substrate 901 (e.g., approximately 300 nm) in the etched region from the process 936, e.g., by DRIE technique, in which a portion of the etched region aligns with the etched region from the process 934 such that there is a cavity through the multi-layered structure. The method includes a process 938 that produces the fabricated integrated silicon microprobe component structure.

Figure 10:
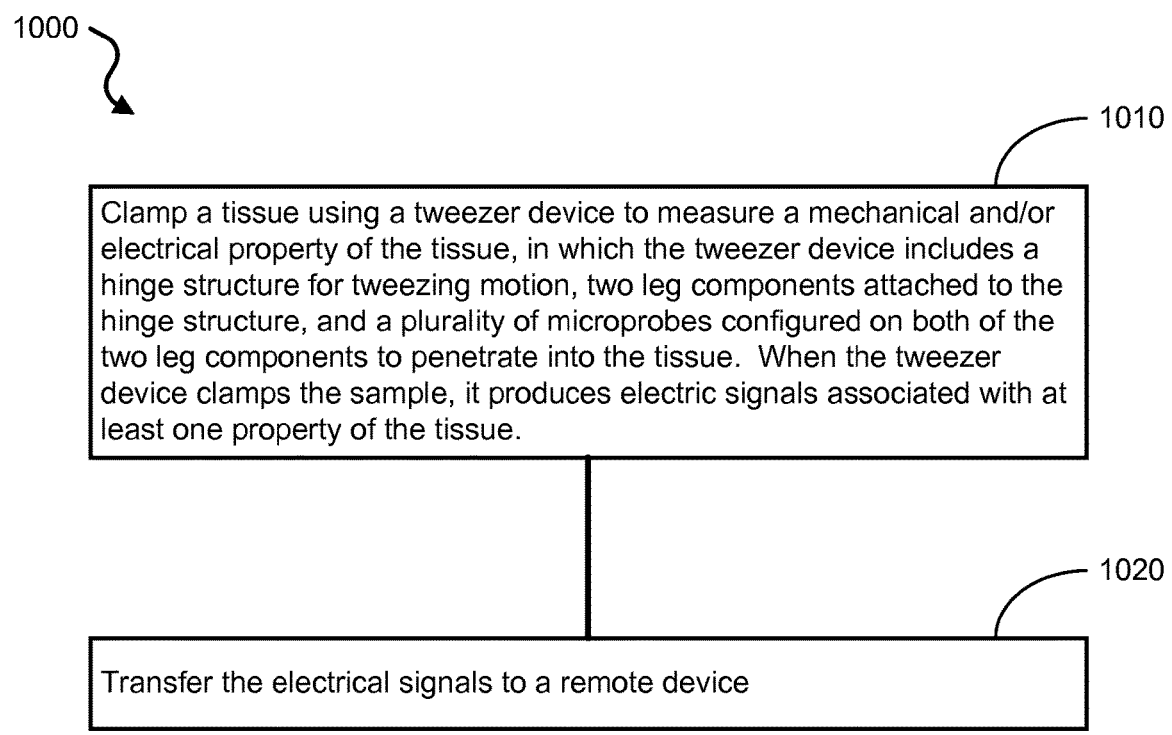
FIG. 10 shows a block diagram of an exemplary method to characterize a property of biological tissue.

In another aspect of the disclosed technology, a method to characterize a property of biological tissue is disclosed. A block diagram of the method (referred to as method 1000) is shown in FIG. 10. The method 1000 includes a process 1010 to clamp a tissue using a tweezer device, e.g., such as the device 100 or the device 700, to measure a mechanical and/or electrical property of the tissue, in which the tweezer device includes a hinge structure for tweezing motion, two leg components attached to the hinge structure, and a plurality of microprobes configured on both of the two leg components to penetrate into the tissue. When the tweezer device clamps the sample, it produces electric signals associated with at least one property of the tissue. The method 1000 includes a process 1020 to transfer the electric signals to a remote device.

In some implementations of the method 1000, for example, the process 1020 can include wirelessly transmitting the electrical signals to a receiver of the remote device. For example, the wirelessly transmitting the electrical signals can include converting the electrical signals from analog to digital format and/or modulating the electrical signals as RF signals, and transmitting the RF signals to an RF receiver. In some implementations, for example, the method 1000 can further include a process to amplify the electrical signals prior to the process 1020 of transferring the electrical signals to the remote device. In some implementations, for example, the method 1000 can further include a process, using a data processing unit, to data process the electric signals to determine at least one of a bioelectrical potential, electrical permittivity, or mechanical compliance of the tissue. For example, the method 1000 can include determining a separation distance between the two leg components by a distance sensor of the tweezer device, in which the distance sensor includes a transducer element operable to transmit sonic pulses at the two leg components, and a receiver element operable to receive the transmitted sonic pulses and to determine the distance between the two leg components. For example, the processing unit can be included on board of the tweezer device and/or on the remote device to implement the data processing.

EXAMPLES

The following examples are illustrative of several embodiments of the present technology. Other exemplary embodiments of the present technology may be presented prior to the following listed examples, or after the following listed examples.

In one example of the present technology (example 1), a tweezer device includes a hinge structure to enable tweezing motion of the device; two leg components coupled to the hinge structure for clamping a sample; a first microprobe and a second microprobe, both configured on both of the two leg components, in which the first and the second microprobe include sensors in a sensing tip structured to penetrate into the sample when the device clamps the sample and produce electric signals from the sensors of a property of the sample, the sensors of the sensing tip including at least one of an electrode to measure an electrical potential, an electrical permittivity sensor to measure electrical permittivity, or a strain gauge to measure mechanical compliance; and an electronic circuit electrically coupled to the first and second microprobes and including a transmitter to wirelessly transmit the electric signals to a remote receiver.

Example 2 includes the device as in example 1, in which the hinge structure, the leg components, and the first and second microprobes include a semiconductor material.

Example 3 includes the device as in example 2, in which the semiconductor material includes silicon.

Example 4 includes the device as in example 1, further including a distance sensor to determine a separation distance between the two leg components, in which the distance sensor includes a transducer element operable to transmit sonic pulses at the two leg components, and a receiver element operable to receive the transmitted sonic pulses and to determine the distance between the two leg components.

Example 5 includes the device as in example 4, in which the electronic circuit includes a processing unit to process the electric signals measured by the first and second microprobes and the separation distance between the two leg components as data to determine stiffness property of the sample.

Example 6 includes the device as in example 4, in which the distance sensor includes a plurality of piezoelectric traducer elements, and in which the piezoelectric transducer elements are configured to actuate the device to cut at least a portion of the sample based on oscillating motion of the piezoelectric transducer elements operating in one or more resonance modes based on a control signal provided by the processing unit.

Example 7 includes the device as in example 4, in which the distance sensor includes a plurality of piezoelectric traducer elements, and in which the piezoelectric transducer elements are configured to actuate the device to sonically measure the stiffness of the sample based on oscillating motion of the piezoelectric transducer elements operating in one or more resonance modes based on a control signal provided by the processing unit.

Example 8 includes the device as in example 1, in which the electronic circuit includes a processing unit to process the electric signals to determine a quantitative value for at least one of the electrical potential, electrical permittivity, or mechanical compliance of the tissue.

Example 9 includes the device as in example 1, in which the electronic circuit includes a solar cell power unit to convert light into electrical energy for powering the sensors of the device.

Example 10 includes the device as in example 1, in which the electrical permittivity sensors of the microprobes provide capacitance measurement signals at discrete steps under different frequencies.

Example 11 includes the device as in example 1, in which the electrodes of the microprobes include platinum.

Example 12 includes the device as in example 1, in which the first microprobe includes the electrical permittivity sensor and the strain gauge, and the second microprobe includes the electrode and the strain gauge.

Example 13 includes the device as in example 1, in which the electronic circuit is configured on the leg components.

Example 14 includes the device as in example 1, further including one or more arm components coupled to the leg components and structured to include the electronic circuit.

Example 15 includes the device as in example 1, further including a support casing to encapsulate at least a portion of the hinge structure and the leg components and provide added structural rigidity to the device.

Example 16 includes the device as in example 1, in which the sample includes biological tissue.

In one example of the present technology (example 17), a method to characterize a property of biological tissue includes clamping a tissue with a tweezer device structured to include a hinge structure to allow tweezing motion of the tweezer device, two leg components attached to the hinge structure, and a plurality of microprobes configured on both of the two leg components to penetrate into the tissue when the tweezer device clamps the sample and produce electric signals associated with at least one property of the tissue. The method includes transferring the electric signals to a remote device.

Example 18 includes the method as in example 17, in which the transferring the electrical signals includes wirelessly transmitting the electrical signals to a receiver of the remote device.

Example 19 includes the method as in example 18, in which the wirelessly transmitting the electrical signals includes modulating the electrical signals as RF signals and transmitting the RF signals to an RF receiver.

Example 20 includes the method as in example 17, further including amplifying the electrical signals prior to the transferring to the remote device.

Example 21 includes the method as in example 17, further including processing the electric signals to determine at least one of a bioelectrical potential, electrical permittivity, or mechanical compliance of the tissue.

Example 22 includes the method as in example 21, further including determining a separation distance between the two leg components by a distance sensor of the tweezer device, in which the distance sensor includes a transducer element operable to transmit sonic pulses at the two leg components, and a receiver element operable to receive the transmitted sonic pulses and to determine the distance between the two leg components.

Example 23 includes the method as in example 22, in which the processing is implemented by the tweezer device; the tweezer device further includes a processing unit to process the electric signals measured by the microprobes and the separation distance between the two leg components as data to determine stiffness property of the sample.

In one example of the present technology (example 24), a tweezer device includes a hinge structure to provide a spring for tweezing motion of the tweezer device; two leg components coupled to the hinge structure; one or more arm components coupled to the leg components and structured to include an electronic interface unit to transmit detected electronic signals as an RF signal to an RF receiver; an array of microprobes configured at an end of one or both leg components away from the hinge structure and operable to measure mechanical and electrical properties of a sample clamped by the tweezer device, the microprobes structured to include protruding regions comprising electrical permittivity sensors, electrode sensors, and polysilicon strain gauges to provide the detected electronic signals by the microprobe to the electronic interface; a transducer element operable to transmit sonic pulses at the two leg components; and a receiver element operable to receive the transmitted sonic pulses and to determine the distance between the two leg components.

Example 25 includes the device as in example 24, in which the polysilicon strain gauges are connected in a Wheatstone bridge configuration.

Example 26 includes the device as in example 24, in which the electrical permittivity sensors provide capacitance measurement signals at discrete steps under different frequencies.

Example 27 includes the device as in example 24, in which the electrode sensors include platinum recording electrodes to provide bio-electrical potential signals.

Example 28 includes the device as in example 24, in which the receiver element includes passive LC components to receive, filter, and rectify the transmitted sonic pulses to form a received pulse modified in amplitude and time-of-arrival.

Example 29 includes the device as in example 24, in which the protrusion regions are structured to include the electrical permittivity sensors or the electrode sensors coupled to the polysilicon strain gauges.

Example 30 includes the device as in example 24, further including a processing unit to process the detected electronic signals by the microprobe and the determined distance between the two leg components as data to determine mechanical or electrical properties of a sample clamped by the tweezer device.

Example 31 includes the device as in example 30, in which the sample includes biological tissue.

Example 32 includes the device as in example 30, in which the data includes force signal versus leg-gap.

Example 33 includes the device as in example 30, in which the determined mechanical properties include stiffness of the sample.

Example 34 includes the device as in example 24, in which the hinge structure, the leg components, and the microprobes include a silicon.

Implementations of the subject matter and the functional operations described in this patent document and attachments can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document and attachments contain many specifics, these should not be construed as limitations on the scope of any invention or of what may be claimed, but rather as descriptions of features that may be specific to particular embodiments of particular inventions. Certain features that are described in this patent document and attachments in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attachments should not be understood as requiring such separation in all embodiments.

Only a few implementations and examples are described and other implementations, enhancements and variations can be made based on what is described and illustrated in this patent document and attachments.

What is claimed is:

1. A tweezer device, comprising: a hinge to enable tweezing motion of the tweezer device;
   a first leg and a second leg coupled to the hinge configured to clamp a sample; a first microprobe and a second microprobe coupled to the first leg and the second leg, respectively, wherein the first microprobe and the second microprobe include sensors in a sensing tip configured to penetrate into the sample when the tweezer device clamps the sample and produce electric signals from the sensors of a property of the sample, the sensors of the sensing tip including at least one of an electrode to measure an electrical potential, an electrical permittivity sensor to measure electrical permittivity, or a strain gauge combined with a distance sensor to measure elastic properties of the sample;
   an electronic circuit electrically coupled to the first and second microprobes and including a transmitter to wirelessly transmit the electric signals to a remote receiver; and
   an arm including the electronic circuit coupled to one of the first leg and the second leg.

2. The device as in claim 1, wherein the hinge, the first leg and the second leg, and the first and second microprobes include a semiconductor material.

3. The device as in claim 2, wherein the first microprobe and the second microprobe include a plurality of microscale sensors.

4. The device as in claim 1, wherein the distance sensor is configured to determine a separation distance between the first leg and the second leg, the distance sensor including: a transducer operable to transmit sonic pulses at the first leg and the second leg, and a receiver operable to receive the transmitted sonic pulses and to determine the distance between the first leg and the second leg.

5. The device as in claim 4, wherein the electronic circuit includes a processing unit to process the electric signals measured by the first and second microprobes and the separation distance between the first leq and the second leg data to determine stiffness property of the sample.

6. The device as in claim 4, wherein the distance sensor includes a plurality of piezoelectric transducers, wherein the piezoelectric transducers are configured to actuate the device to cut at least a portion of the sample based on oscillating motion of the piezoelectric transducers operating in one or more resonance modes based on a control signal provided by a processing unit.

7. The device as in claim 4, wherein the distance sensor includes a plurality of piezoelectric transducers, wherein the piezoelectric transducers are configured to actuate the device to sonically measure a stiffness of the sample based on oscillating motion of the piezoelectric transducers operating in one or more resonance modes based on a control signal provided by a processing unit.

8. The device as in claim 1, wherein the electronic circuit includes a processor configured to process the electric signals to determine a quantitative value for at least one of the electrical potential, electrical permittivity, or pressure based on deformation of the strain gauge.

9. The device as in claim 1, wherein the electronic circuit includes a solar cell to convert light into electrical energy for powering the sensors of the device.

10. The device as in claim 1, wherein the electrical permittivity sensors of the microprobes provide capacitance measurement signals at discrete steps under different frequencies.

11. The device as in claim 1, wherein the first microprobe includes the electrical permittivity sensor and the strain gauge, and the second microprobe includes the electrode and the strain gauge.

12. The device as in claim 1, wherein the electronic circuit is coupled to one of the first leg and the second leg.

13. The device as in claim 1, further comprising:
a support casing to encapsulate at least a portion of the hinge and the first leg and the second leg, the support casing providing rigidity to the tweezer device.

14. The device as in claim 1, wherein the sample includes biological tissue.

15. The device of claim 1, wherein the electronic circuit is on a printed circuit board (PCB).

16. The device of claim 1, wherein the hinge is a deformable curved, circular, or loop-shaped hinge.

17. The device of claim 1, wherein the distance sensor is a sonar sensor or a permittivity sensor wherein the permittivity sensor measures distance by measuring the capacitance between the microprobes.

18. A method to characterize a property of a sample, comprising:
clamping a sample with a tweezer device including a hinge to allow tweezing motion of the tweezer device, a first leg and a second leg attached to the hinge, and a plurality of microprobes configured on both the first leg and the second leg, the plurality of microprobes configured to penetrate into the sample when the tweezer device clamps the sample and produce electric signals associated with at least one property of the sample;
measuring at least one of an electric potential using an electrode or an electrical permittivity using an electrical permittivity sensor or elastic properties of the sample using a strain gauge combined with a sensor, wherein the electrode or the electrical permittivity sensor or the strain gauge are positioned on the plurality of microprobes;
transferring the electric signals to a remote device with an electronic circuit coupled to the tweezer device, wherein the electronic circuit is positioned on an arm coupled to one of the first leg or the second leg.

19. The method of claim 18, wherein the transferring the electrical signals includes wirelessly transmitting the electrical signals with the electronic circuit to a receiver of the remote device.

20. The method of claim 19, wherein the wirelessly transmitting the electrical signals includes modulating the electrical signals into RF signals and transmitting the RF signals to an RF receiver.

21. The method of claim 18, further comprising:
amplifying the electrical signals prior to the transferring to the remote device.

22. A tweezer device, comprising:
a hinge to enable tweezing motion of the tweezer device:
a first leg and a second leg coupled to the hinge configured to clamp a sample: a first microprobe and a second microprobe coupled to the first leg and the second leg, respectively, wherein the first microprobe and the second microprobe include sensors in a sensing tip configured to penetrate into the sample when the tweezer device clamps the sample and produce electric signals from the sensors of a property of the sample, the sensors of the sensing tip including at least one of an electrode to measure an electrical potential, an electrical permittivity sensor to measure electrical permittivity, or a strain gauge combined with a distance sensor to measure elastic properties of the sample: and
an electronic circuit electrically coupled to the first and second microprobes and including a transmitter to wirelessly transmit the electric signals to a remote receiver:
wherein one terminal end of the first leg is attached to the hinge at one terminal end of the hinge and one terminal end of the second leg is attached to the hinge at another terminal end of the hinge.

23. The device as in claim 22, wherein the hinge, the first leg and the second leg, and the first and second microprobes include a semiconductor material.

24. The device as in claim 23, wherein the first microprobe and the second microprobe include a plurality of microscale sensors.

25. The device as in claim 22, wherein the electronic circuit includes a processor configured to process the electric signals to determine a quantitative value for at least one of the electrical potential, electrical permittivity, or pressure based on deformation of the strain gauge.

26. The device as in claim 22, wherein the electronic circuit includes a solar cell to convert light into electrical energy for powering the sensors of the device.

27. The device as in claim 22, wherein the electrical permittivity sensors of the microprobes provide capacitance measurement signals at discrete steps under different frequencies.

28. The device as in claim 22, wherein the first microprobe includes the electrical permittivity sensor and the strain gauge, and the second microprobe includes the electrode and the strain gauge.

29. The device as in claim 22, wherein the electronic circuit is coupled to one of the first leg and the second leg.

30. The device as in claim 22, further comprising:
a support casing to encapsulate at least a portion of the hinge and the first leg and the second leg, the support casing providing rigidity to the tweezer device.

31. The device as in claim 22, wherein the sample includes biological tissue.

32. The device of claim 22, wherein the electronic circuit is on a printed circuit board (PCB).

33. The device of claim 22, wherein the hinge is a deformable curved, circular, or loop-shaped hinge.

34. The device of claim 22, wherein the distance sensor is a sonar sensor or a permittivity sensor wherein the permittivity sensor measures distance by measuring the capacitance between the microprobes.

* * * * *